US011737955B2

(12) United States Patent
Kishen et al.

(10) Patent No.: US 11,737,955 B2
(45) Date of Patent: Aug. 29, 2023

(54) MULTI-FUNCTIONAL MICRO AND NANOPARTICLES FOR USE IN ROOT CANAL THERAPIES

(71) Applicant: THE GOVERNING COUNCIL OF THE UNIVERSITY OF TORONTO, Toronto (CA)

(72) Inventors: Anil Kishen, Mississauga (CA); Annie Shrestha, Toronto (CA)

(73) Assignee: Anil Kishen, North York (CA)

( * ) Notice: Subject to any disclaimer, the term of this patent is extended or adjusted under 35 U.S.C. 154(b) by 581 days.

(21) Appl. No.: 15/932,180

(22) Filed: Feb. 16, 2018

(65) Prior Publication Data

US 2018/0185249 A1    Jul. 5, 2018

Related U.S. Application Data

(60) Division of application No. 15/264,364, filed on Sep. 13, 2016, now abandoned, which is a continuation of application No. 14/385,596, filed as application No. PCT/CA2013/000275 on Mar. 21, 2013, now abandoned.

(60) Provisional application No. 61/614,235, filed on Mar. 22, 2012.

(51) Int. Cl.
| | |
|---|---|
| *A61K 6/00* | (2020.01) |
| *A61K 6/62* | (2020.01) |
| *A61C 5/40* | (2017.01) |
| *A61C 5/55* | (2017.01) |
| *A61K 41/00* | (2020.01) |
| *A61K 9/51* | (2006.01) |
| *A61K 6/17* | (2020.01) |
| *A61K 6/52* | (2020.01) |
| *A61K 6/54* | (2020.01) |
| *A61K 6/65* | (2020.01) |
| *A61N 5/06* | (2006.01) |

(52) U.S. Cl.
CPC ............... *A61K 6/62* (2020.01); *A61C 5/40* (2017.02); *A61C 5/55* (2017.02); *A61K 6/17* (2020.01); *A61K 6/52* (2020.01); *A61K 6/54* (2020.01); *A61K 6/65* (2020.01); *A61K 9/5161* (2013.01); *A61K 41/0057* (2013.01); *A61N 5/062* (2013.01)

(58) Field of Classification Search
None
See application file for complete search history.

(56) References Cited

U.S. PATENT DOCUMENTS

| | | | |
|---|---|---|---|
| 2003/0113686 A1 | 6/2003 | Jia et al. | |
| 2005/0226938 A1 | 10/2005 | Borbely et al. | |
| 2005/0281886 A1 | 12/2005 | Cattaneo | |
| 2009/0220908 A1 * | 9/2009 | Divito ............... | A61C 1/0046 433/29 |
| 2010/0330523 A1 | 12/2010 | Kert | |

FOREIGN PATENT DOCUMENTS

| | | |
|---|---|---|
| JP | 04230612 A | 8/1992 |
| JP | 05220214 A | 8/1993 |
| JP | 07112023 A | 5/1995 |
| WO | 2006096893 A2 | 9/2006 |
| WO | WO-2011006263 A1 * | 1/2011 ........... A61K 41/008 |

OTHER PUBLICATIONS

Xu et al. J. of Biomedical Materials Research Part B: Applied Biomaterials, 2011, 98B(1), 150-159 (Year: 2011).*
Tsai et al. (Antimicrobial Agents and Chemotherapy, 55(5), p. 1883-1890, 2011, newly cited) Chitosan Augments Photodynamic Inactivation of Gram-Positive and . . . .*
Rolim et al. (Journal of Photochemistry and Photobiology B: Biology 106 (2012) 40-4641, available online Oct. 19, 2011, newly cited) The antimicrobial activity of photodynamic therapy against *Streptococcus* mutans using . . . .*
Madhavan et al. (Acta Biomaterialia 6 (2010) 1413-1422) Evaluation of composition and crosslinking effects on collagen-based composite constructs.*
Kishen, A. Advanced therapeutic options for endodontic biofilms. Endodontic Topics; 22(1), 99-123, 2010.
Kishen, A. & Haapasalo M. Biofilm models and methods of biofilm assessment. Endodontic Topics: 22, 58-78, 2012.
Shrestha, A. & Kishen A. Antibacterial efficacy of a photosensitizer functionalized biopolymeric nanoparticles in the presence of tissue inhibitors in root canal. Journal of Endodontics Apr. 2014;40(4):566-70 [Impact factor: 3.122].
Shrestha, A et al. Photo-Activated Polycationic Bioactive Chitosan Nanoparticles Inactivate Bacterial Endotoxins. Journal of Endodontics Jan. 2015. pii: 50099-2399(14)01217-5.
Li FC & Kishen, A. Micro-tissue engineering root canal dentine with cross-linked biopolymeric nanoparticles for mechanical stabilization. International Endodontic Journal Oct. 2018;51(10):1171-1180.
Li FC et al. Microtissue Engineering Root Dentin with Photodynamically Cross-linked Nanoparticles Improves Fatigue Resistance of Endodontically Treated Teeth. Journal of Endodontics Mar. 12, 2020. pii: 50099-2399(20)30074-1.
Hashmi, A. et al. Impact of Dentin Substrate Modification with Chitosan-Hydroxyapatite Precursor Nanocomplexes on Sealer Penetration and Tensile Strength Journal of Endodontics, Jul. 2019;45(7):935-942.
Hashmi, A. et al. Interfacial Characterization of Dentin Conditioned with Chitosan Hydroxyapatite precursor Nanocomplexes using Time-of-Flight Secondary Ion Mass Spectrometry. Journal of Endodontics Oct. 5, 2019. pii: S0099-2399(19)30625-9.

(Continued)

*Primary Examiner* — Tigabu Kassa

(57) ABSTRACT

Chitosan nanoparticles are provided for use in the in vivo treatment of connective tissues in root canal therapies. The nanoparticles are optionally linked with one or more photoactivatable compounds for providing antibacterial/antibiofilm properties, neutralizing bacterial byproducts and/or chemical/photodynamic crosslinking to achieve enhanced mechanical properties, chemical stability in connective tissues and/or to improve surface/interfacial integrity between filling material and connective tissue.

12 Claims, 21 Drawing Sheets

(56) References Cited

OTHER PUBLICATIONS

Shrestha, Annie et al. "Photoactivated rose Bengal functionalized chitosan nanoparticles produce antibacterial biofilm activity and stabilize dentin-collagen" Nanomedicine: Nanotechnology, Biology, and Medicine, vol. 10, Issue 3, Apr. 2014, pp. 491-501.

Shrestha, A. et al. "Antibiofilm Efficacy of Photosynthesizer-functionalized Bioactive Nanoparticles on Multispecies Biofilm", Journal of Endodontics, vol. 40, Issue 10, published Oct. 2014, pp. 1604-1610, American Associate of Endodontists.

Shrestha, A et al. "Polycationic Chitosan-Conjugated Photosensitizer for Antibacterial Photodynamic Therapy" Photochemistry and Photobiology 2012, 88, 577-583, Wiley Periodical Inc.

Shrestha, A. et al. "Characterization of a Conjugate between Rose Bengal and Chitosan for Targeted Antibiofilm and Tissue Stabilization Effects as a Potential Treatment for Infected Dentin" Antimicrobial agents and Chemotherapy 2012, 56(9), 4876-4884. Published ahead of print Jul. 9, 2012.

Shrestha. A. et al. "The Effect of Tissue Inhibitors on the Antibacterial Activity of Chitosan Nanoparticles and Photodynamic Therapy" Journal of Endodontics 2012, 38(9), 1275-1278. Published Sep. 2012 (Sep. 2012) American Associate of Endodontists.

Kishen, A. et al. "An Investigation on the Antibacterial and Antibiofilm Efficacy or Cationic Nanoparticles for Root Canal Disinfection" Journal of Endodontics 2008, 34(12), 1515-1520; American Association of Endodontists.

Shrestha, A. et al. "Photodynamically Crosslinked and Chitosan-incorporated Dentin Collagen" Journal of Dental Search 2011, 90(11), 1346-1351. Published online Sep. 12, 2011; International & American Associations for Dental Research.

Bojar, W. et al. "Formation and preclinical evaluation of a new alloplastic bone substitute material" Acta of Bioengineering and Biomechanics 2012, 14(1), 39-44.

Chitosan structure, hindawi.com (http://www.hindawi.com/journals/ijcc/2011/865704/fig1/), 2011, no pagination.

Konopka, K.; et al. "Photodynamic therapy in dentistry" Journal of Dental Research, 2007, 86(8) 694-707.

George, S; et al. "Calcium phosphate cement: a new saviour for furcation perforation?—an in-vitro study" https://web.archive.org/web/20090416220622/http://medind.nic.in/eaa/t06/i1/eaat06i1p7.pdf, cached wayback machine 2009, pp. 7-11.

Moczek, L.; et al. "Novel Water-soluble photosensitizers from Chitosan" Biomacromolecules, 2007, 8, 433-438.

Wang, X.; et. al. "Structural characterization of phosphorylated chitosan and their applications as effective additives of calcium phosphate cements" Biomaterials, 2001, 22, 2247-2255.

International Preliminary Report on Patentability for related international application No. PCT/CA2013/000275, dated Oct. 2, 2014.

* cited by examiner

MULTI-FUNCTIONAL MICRO AND NANOPARTICLES FOR USE IN ROOT CANAL THERAPIES

RELATED APPLICATIONS

This application is a continuation of U.S. patent application Ser. No. 14/385,596, which is the national phase application claiming the benefit of PCT/CA2013/000275 filed 21 Mar. 2013, in English, which further claims the benefit of 35 USC § 119(e) to U.S. Provisional Application Ser. No. 61/614,235 filed 22 Mar. 2012.

SCOPE

The invention relates to nanoparticles for use in the in vivo treatment of connective tissues in root canal therapies, and more particularly chitosan polymer nanoparticles which may optionally be linked with one or more photoactivatable compounds for providing antibacterial/antibiofilm, neutralize bacterial byproducts and/or chemical/photodynamic crosslinking to achieve enhanced mechanical properties, chemical stability in connective tissues and/or chemicals to improve surface/interfacial integrity between filling material and connective tissue.

BACKGROUND

Root canal or endodontic therapies involve the physical removal of the tooth root pulp by using successively larger helical dental files and reamers. The files and reamers penetrate and remove the pulp tissue leaving a hollowed-out root canal or opening which is bordered by exposed dentin. The root canal preparation extends to the apical tip of the root to allow infection drainage and prevent re-infection. In conventional root canal therapies following removal of the dental pulp and cleaning, a suitable packing material, such as gutta-percha rubber, is inserted into the hollowed-out root canal in conjunction with a cement and/or sealer, and thereafter heat fused in place. After the gutta-percha filing, the tooth is covered with a crown, amalgam, or composite dental restoration filling material.

Because the infection and subsequent removal of the highly hydrated vascularized dental pulp tends to weaken the remaining dentin structure, teeth which undergo endodontic therapies may be more prone to fracture and root failure. In addition, the surrounding dentin itself is generally subject to infection infiltration from the infected pulp, via dentinal tubules.

In endodontic treatments, infected hard tissues within the root dentin are typically managed using antimicrobial agents which are selected to eliminate causative microorganisms. Conventional treatment approaches frequently result in the incomplete elimination of microbes which reside within the complexities of the root dentin. As well, conventional antimicrobial agents may result in treatment induced changes in the mechanical characteristics of the dentin tissue surrounding the hollowed-out root canal, as well as degradation of the infected dentin tissues due to host and/or bacterial derived proteases. Degradation of the hard dentin tissues may further result in a significant decrease of mechanical tooth strength. While various alternative antimicrobial approaches to achieve effective root dentin disinfection have been proposed, heretofore, conventional root therapies have not addressed the improvement of mechanical properties of infected hard tissues.

Photodynamic therapy involving the exposure of tissues to selected light energies has been adopted for use in multiple treatment applications, including antibacterial disinfection, anticancer therapies, tissue welding and tissue engineering. A combination of a light-activatable chemicals (photosensitizers), appropriate light energy (UV) and oxygen are often important factors in photodynamic therapy (PDT) based treatments. With photodynamic therapy, the photosensitizer is excited by illumination with appropriate wavelength and goes to a higher-energy 'triplet state' from a lower-energy 'ground state'. Most typically, the excited photosensitizer molecules transfer electrons to neighboring molecules (type-1 reaction) to generate radical oxygen species, or its energy to the ground state molecular oxygen (type-2 reaction) to generate highly reactive oxygen species (ROS), and most typically singlet oxygen.

Photodynamic therapy may also be useful in biomedicine for the photodynamic crosslinking of proteins and collagen. The singlet oxygen produced facilitates formation of inter and intramolecular covalent crosslinks in collagen molecules and other available active sites in the presence of appropriate photosensitizers such as Rose Bengal (RB). Photodynamic crosslinking is a rapid process, resulting from the generation of reactive oxygen species and formation of covalent collagen crosslinks in a light-independent manner. Covalent coupling between free amino groups and photo-oxidized amino acids have been proven by the decrease in reactivity and available free amino groups following photodynamic crosslinking in the presence of a sensitizer. The formation of additional crosslinks resulted in improved biological and mechanical properties of collagen structures. Incorporation and crosslinking of biopolymers, such as elastin and chitosan (CS) with collagen advantageously may reinforce the collagen scaffolds. Photosensitizer solutions are however, generally known to be susceptible to leaving residual traces after photoactivation, which may not be acceptable in the in vivo treatment of tissues or applications.

The uptake of anionic and cationic photosensitizers is known to occur via different mechanisms. Anionic photosensitizers such as Rose Bengal adhere only superficially. Deeper penetration into bacterial cells or through the highly negative extracellular polysaccharide is not possible and uptake may be increased in the presence of divalent cations. Conjugation of anionic photosensitizers with poly-lysine and polymyxin B nonapeptide have been tried to increase the antibacterial efficacy against both gram-positive and gram-negative bacteria. Immobilization of Rose Bengal on polystyrene beads has also shown antibacterial properties when irradiated. Although photosensitizers have been conjugated with different readily available synthetic polymers and liposomes, these also possess a significant limiting factor of biocompatibility when applied in-vivo.

SUMMARY

The applicant has appreciated that the immobilization of photosensitizers on polymeric supports could avoid or minimize the formation of residual photosensitizers, making such compounds more suitable for use in in vivo. Further, immobilization of polymeric supports may also provide the added advantage of enhanced stability in case of physiologic environments. Although photosensitizers have been conjugated with different readily available synthetic polymers and liposomes, these possess a significant limiting factor of biocompatibility when applied in vivo. The applicant has recognized that the use of naturally occurring biopolymers, such as chitosan may however counteract the biocompatibility issues.

Chitosan is a linear polysaccharide, a derivative of chitin, is an abundant natural biopolymer, and has received significant interest for use in biomedicine, food industries, agriculture and environmental fields. Chitosan shows a broad range of antimicrobial activity, biocompatible and biodegradable properties. The chitosan polymers with its large number of free hydroxyl and amino groups has been used for various chemical modifications and grafting. Chitosan polymers are wettable, favouring intimate contact between the sensitized surface or photosensitizer and aqueous suspensions of microorganisms. Chitosan polymers are also considered to be structurally similar to extracellular matrix components and can be used to reinforce collagen constructs.

A disadvantage of chitosan is its low solubility at a physiological pH of 7.4 due to its rigid crystalline structure and primary amino group residues. However, the applicant has appreciated that conjugation of chitosan with photosensitizers such as Rose Bengal, or other anionically or cationically charged photosensitizers may result in water-soluble particles at even higher pH levels.

Accordingly, one objective of the present invention provides for an antibacterial composition for use in vivo in pre-treating hard and/or connective tissues to minimize and/or reduce the possibility of bacterial infection/reinfection therethrough. In addition, it is also known that chitosan requires (more than 24 hours) to eliminate free-floating bacteria and is not able to disrupt bacterial biofilms, which is important in the treatment of root canal treatment.

Another objective of the invention is to provide a composition for enhancing the fracture toughness and/or mechanical strength of hard and/or connective tissues in the body, and more preferably dentin tissues.

A further object of the invention is to provide improved nanoparticles having a size selected at less than about 100 nanometers, and preferably from about 60 nanometers to 90 nanometers, and which are suitable for use in sealing and/or strengthening hard connective tissues in the body, and more preferably strengthening tooth dentin as part of restorative endodontic or restorative treatments.

In one aspect, the present invention utilizes multifunctional chitosan-based particles which preferably have micro/nano dimensions of up to 150 nanometers, preferably less than about 100 microns and most preferably about 60 to about 90 nanometers, and which are preferably admixed with a pharmaceutically acceptable carrier. The particles may or may not be photoactivatable, whereby exposure to light energy and preferably a selected light energy (for example in green light) may be used to effect crosslinking and/or generate antibacterial radical oxygen species. In one preferred use, the composition is to be applied to a root canal wall/dentin of a tooth following root exposure or an endodontic root procedure, and before filling of the sealer and root canal obturation material, such as gutta-percha rubber.

In another preferred use, the invention provides for the in vivo application to hard or connective tissues of a composition comprising chitosan and/or chitosan-based derivatives in micronized particle form, and preferably a composition which comprises chitosan-based particles in an amount of 0.3 to 1% (by weight). More preferably, the chitosan based nanoparticles are conjugated/functionalized with a photoactivatable carrier, such as Rose Bengal for use to:

(a) Inactivate and/or inhibit activation of residual microbes and biofilms;
(b) Inhibit hard tissue, and preferably dentin surface degradation (resorption) by enhancing its chemical stability;
(c) Inhibit microbial re-entry (bacterial adherence, bacterial penetration via interfaces into hard and/or connective tissue);
(d) Improve mechanical integrity of connective and/or hard tissue, and preferably dentin (fracture toughness); and/or
(e) Improve connective tissue or dentin-obturating material interface by biomineralization.

More preferably, the invention provides bioreactive micro or nanoparticles for use in inhibiting one or more of the prevention of bacterial persistence, bacterial reentry/recolonization, ultrastructural changes, degradation and/or compromise in the mechanical characteristics of connective or hard tissues, and more preferably dentin in endodontically treated teeth.

In another aspect, the present invention provides multifunctional bioactive micro nanoparticles for use in vivo in the enhancement of one or more antibacterial properties, interfacial integrity and/or fracture toughness of infected dentin hard tissues in root canal therapies.

Chemical or photodynamic crosslinking methods have been used in tissue engineering to stabilize collagenous biological tissues by inducing various intra and intermolecular crosslinks in collagen. The applicant has appreciated dentin as a biocomposite, contributes to the structural stability of the root treated teeth and can be stabilized by collagen crosslinking processes. Apart from the cytotoxicity of glutaraldehyde, the treatment time required to establish stable collagen crosslinks tends to be much longer with chemical crosslinking methods, and is a major limitation especially for in vivo clinical applications, where shorter treatment time is highly desirable and biocompatibility is of concern.

Photodynamic crosslinking advantageously may provide a rapid process that occurs via the production of singlet oxygen or radicals by the light excited photosensitizers. The singlet oxygen interacts with photooxidizable amino acid residues, such as Cysteine, Histidine, Tryptophan or Tyrosine in a protein molecule. The photooxidized products, in turn, react with normal or photoaltered residues in another protein molecule resulting in a crosslink. The addition of polymers, such as chitosan, during collagen crosslinking may advantageously be used in in vivo methods to produce collagen scaffolds in tooth dentin with superior biological and physical properties.

It has been appreciated that nanoparticles of photoactivated chitosan polymer-Rose Bengal (CSRBnp) not only will induce crosslinking of collagen, but also allow covalent bonding of chitosan with the collagen matrix. Accordingly, in another aspect of the invention, chitosan is combined with photosensitizers such as Rose Bengal to aid in developing multifunctional nanoparticles which possess enhanced antibacterial efficacy, induce crosslinking of collagen matrix, and/or facilitate its incorporation into the collagen matrix of the dentin during photoactivation. In addition, the composition could be applied during the restorative treatments and/or the minimally invasive management of dentinal caries.

Chitosan polymer-Rose Bengal nanoparticles provide both the broad range of antimicrobial properties of chitosan and photosensitizer properties of Rose Bengal. Further, nanosized particles having a size selected at between about 60 nm and 90 nm advantageously provide a reactive surface area which increases aiding to the antibacterial effect. Chitosan polymer-Rose Bengal nanoparticles may thus perform dual function of enhanced elimination of bacterial biofilm and improved structural stability/mechanical reinforcement of dentin collagen following photodynamic crosslinking.

Most preferably, the multifunctional chitosan nanoparticles consist of a photosensitizer which is conjugated with chitosan and/or phosphorylated chitosan combined with photo-activation, and which are provided as a compound or in a composition for use in a single step root canal disinfection procedure immediately before root canal filling and sealing.

Accordingly, in one aspect the present invention resides in a composition for use in in vivo disinfection and/or remineralization treatment of connective or hard tissues comprising nanoparticles, said nanoparticles comprising a polysaccharide having a plurality of five or six membered ring carbohydrate monomers, where each said monomer is optionally substituted with at least one of a primary amine and a secondary or tertiary amine having an acyl group with two to seven carbon atoms.

In another aspect, the invention resides in a method of dental restoration whereby following exposure of dentin, contacting the dentin with aforementioned composition.

In a further aspect, the present invention resides in a method of making a medicament for in vivo disinfection and remineralization of hard or connective tissues, comprising: forming a phosphorylated chitosan polymer; and micronizing said phosphorylated chitosan polymer to form nanoparticles having an average size selected at between about 40 microns and about 80 microns, and admixing said nanoparticles with a pharmaceutically acceptable carrier.

In yet another aspect, the present invention resides in a method of making a medicament for in vivo disinfection and remineralization of hard or connective tissues, comprising: forming a phosphorylated chitosan polymer; and micronizing said phosphorylated chitosan polymer to form nanoparticles having an average size selected at up to about 100 nanometers, and preferably between about 60 nanometers and 90 nanometers, and admixing or mixing said nanoparticles with a pharmaceutically acceptable carrier.

The present disclosure provides a composition for endodontic or dental restorative use, comprising:
multifunctional biopolymer-based particles wherein a first portion of biopolymer-based particles have biopolymer repeat units covalently functionalized with photosensitizer moieties and a second portion of the of biopolymer-based particles have biopolymer repeat units covalently functionalized with phosphorylated moieties; and
a pharmaceutically acceptable liquid carrier, wherein the multifunctional biopolymer-based particles are mixed with the pharmaceutically acceptable liquid carrier to form a slurry.

The present disclosure provides a method of dental treatment, comprising:
contacting a dentin of a tooth with a pharmaceutical composition comprising a slurry of biopolymer-based particles wherein a first portion of biopolymer-based particles have biopolymer repeat units covalently functionalized with photosensitizer moieties and a second portion of the of biopolymer-based particles have biopolymer repeat units covalently functionalized with phosphorylated moieties; and
exposing the slurry of biopolymer-based particles to a light having a wavelength selected to activate the photosensitizer moieties for a period of time sufficient to crosslink the biopolymer-based particles functionalized with the photosensitizer moieties to the dentin.

The present disclosure provides a method of dental treatment, comprising:
removing infected pulp tissue from a tooth root and forming a hollowed-out root canal thereby exposing dentin along a substantial length of the hollowed-out root canal;
applying a slurry of biopolymer-based particles to the exposed dentin within the hollowed-out root canal, wherein a first portion of biopolymer-based particles have biopolymer repeat units covalently functionalized with photosensitizer moieties and a second portion of biopolymer-based particles have biopolymer repeat units covalently functionalized with phosphorylated moieties;
exposing the slurry of biopolymer-based particles to a light having a wavelength selected to activate the photosensitizer moieties for a period of time; and
after exposing the slurry to the light, filling the hollowed-out root canal with a filling material.

BRIEF DESCRIPTION OF THE DRAWINGS

Reference may now be had to the following detailed description taken together with the accompanying drawings in which:

FIG. 16 shows there was a significant difference in antibacterial properties achieved by chitosan Rose Bengal nanoparticles as compared to Rose Bengal. The error bars illustrate the standard deviation for the average value;

DETAILED DESCRIPTION

Figure 1:
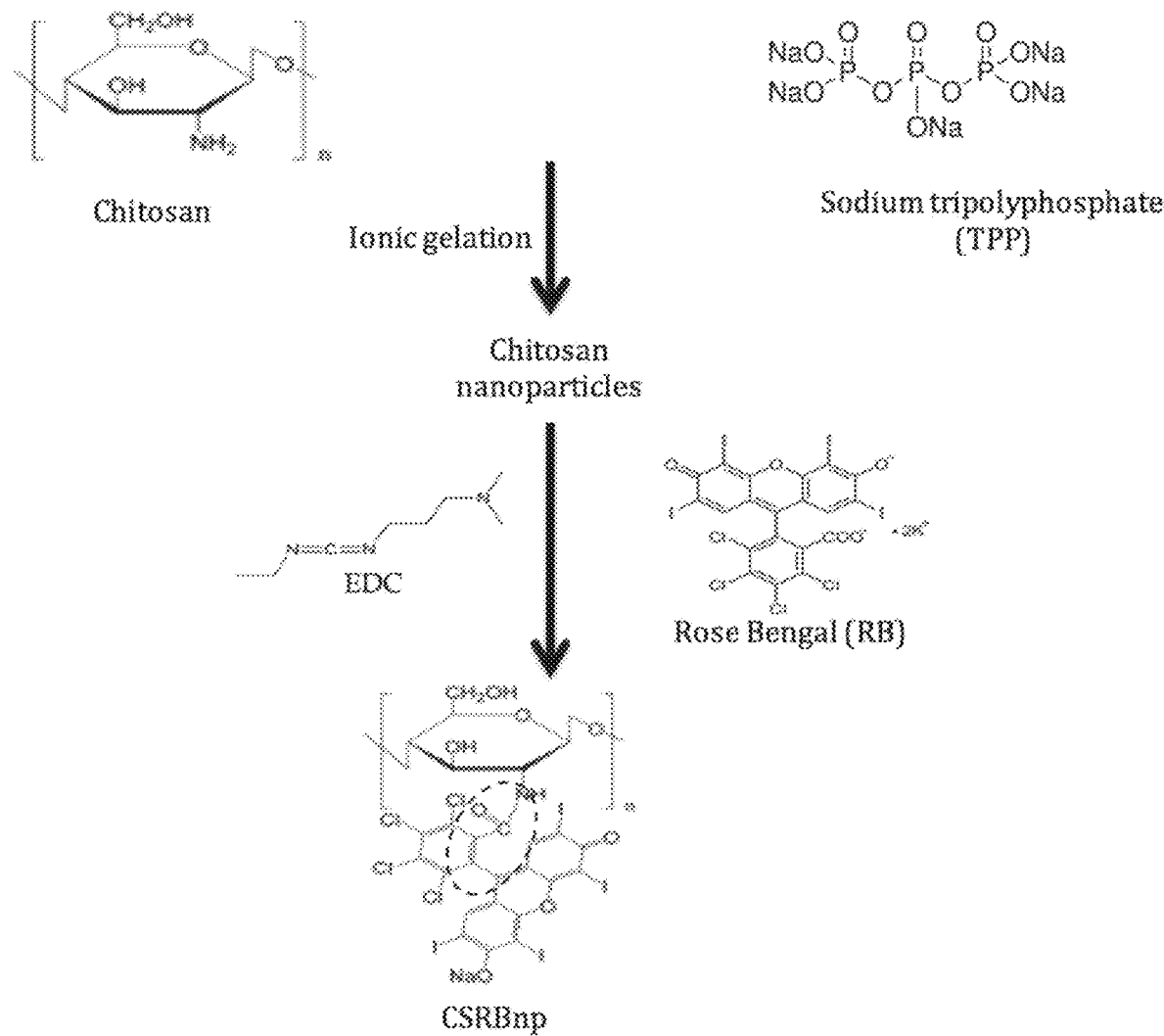
FIG. 1 shows the chemical reaction both during conjugation of chitosan nanoparticles chitosan with Rose Bengal in the presence of EDC (N-ethyl-N'-(3-dimethyl aminopropyl) carbodiimide) and NHS (N-Hydroxysuccinimide), wherein the formation of chemical bonds between the NH group of chitosan and photosensitizers are highlighted with dotted circles.
Figure 2:
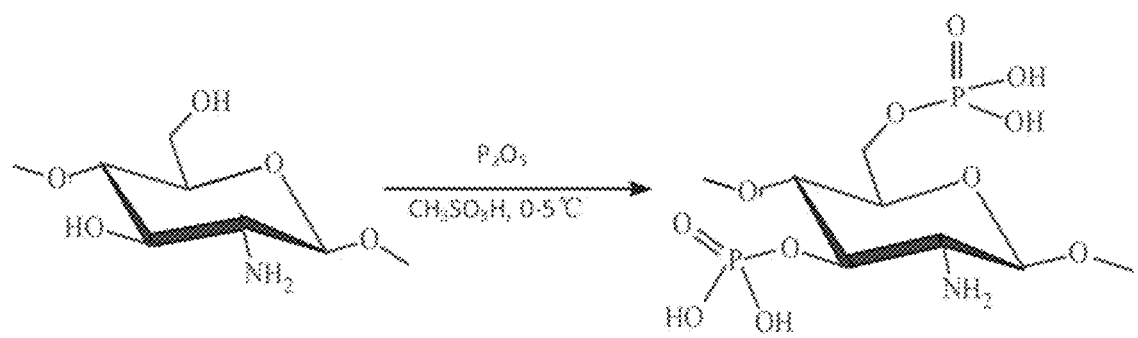
FIG. 2 shows schematically the mechanism of phosphorylation of chitosan.
Figure 3:
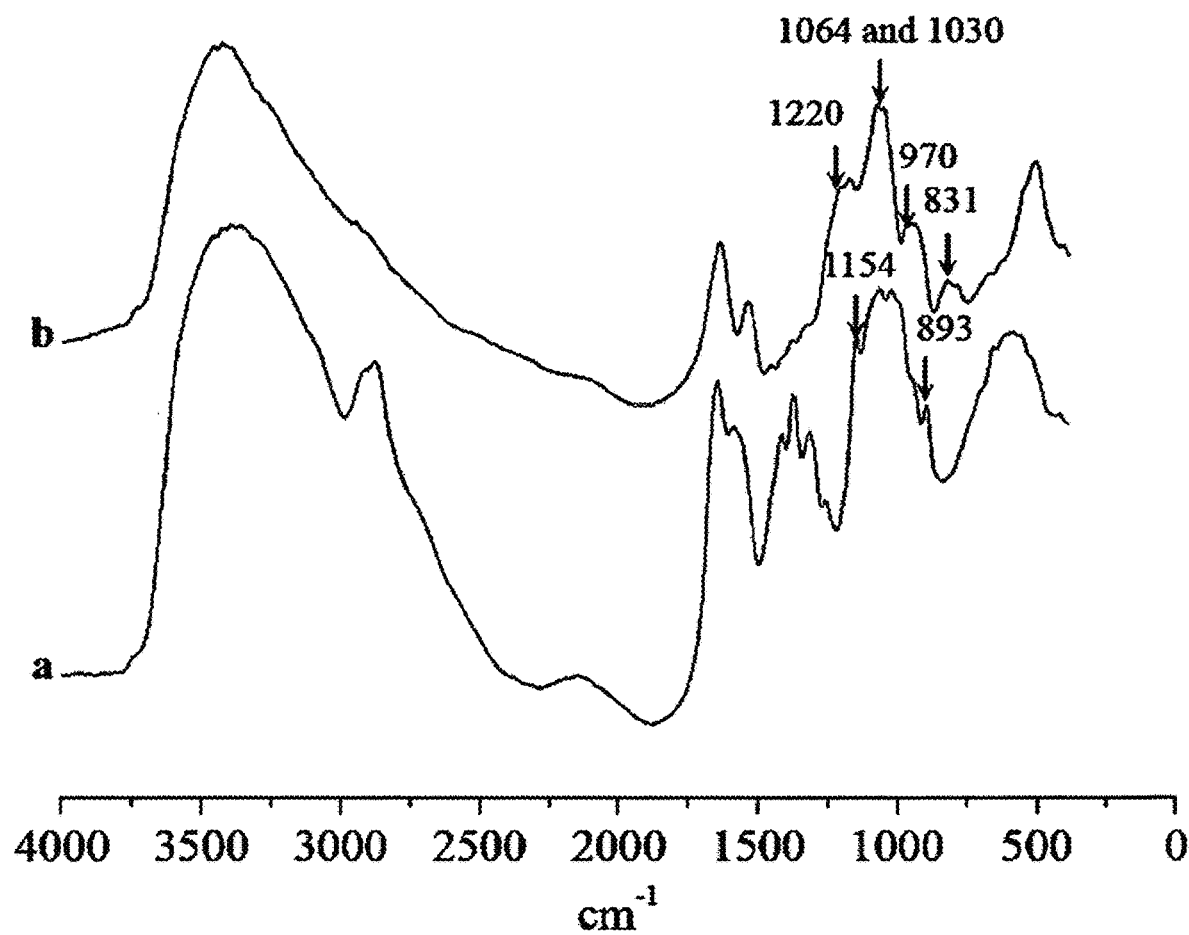
FIG. 3 shows graphically FTIR analysis of phosphorylated chitosan (a) chitosan (b) phosphorylated chitosan.

The present invention provides for a modified polymeric photosensitizer composition that includes photoactivatable nanoparticles of a chitosan polymer which have been conjugated with Rose Bengal as a photosensitizer. Preferably, the nanoparticles have a size selected at up to about 100 nanometers, preferably between about 60 nanometers and 90 nanometers, and more preferably, about 80 nanometers. The particles are preferably admixed with a suitable liquid carrier to form a slurry and which, as will be described, act as an antibacterial and remineralization agent for pre-treating the dentin of hollowed-out root canal, prior to placement and cementation of gutta-percha filler material within the hollowed-out tooth root canal in an endodontic therapy. The carrier may be any one of water and an alcohol.

In an endodontic treatment using the nanoparticles of the present invention, the dental pulp canal is first exposed. The pulp of the infected root is removed using endodontic files in a conventional manner and allowed to drain. Following the pulp removal, the infected material from the root canal is removed and root canal space is shaped using mechanical instruments and chemical irrigants. Once this cleaning and shaping procedure of the root canal system is completed, the nanoparticles slurry (supplied in a packet) can be applied within the root canal space by syringe with or without agitation/activation rising ultrasonic/sonic methods. The chitosan conjugated photosensitizer nanoparticles will be activated using light. A fiber optic cable will be used to deliver light into the root canal is blot-dried using paper points. Following blot-drying the root canal is exposed to light energy having a wavelength selected to photoactivate the nanoparticles for a sufficient period of time to achieve the desired cross linking and/or antibacterial effect. Most preferably, the slurry is exposed to visible light energy for a period of up to 10 minutes and more preferably from about 3 to 8 minutes. After cross-linking, the root canal is filled using conventional root canal obturating/filling material and root canal sealer.

In particular, following the activation of the chitosan polymer Rose Bengal nanoparticles, the root canal is washed.

A gutta-percha cone is coated in a cement mixture of zinc oxide eugenol based cements, methacrylate based cements or epoxy based cements. Thereafter, the coated gutta-percha cone is physically placed within the hollowed-out, cleaned and shaped root. After placement, the case is thermally fused in place using a heated packing tool.

Following root filling with gutta-percha, the exposed dentin pulp chamber is covered with an amalgam or composite filling material, and prosthetic crown thereafter is applied.

In accordance with the preferred application, chitosan polymer-Rose Bengal nanoparticles were synthesized and their potential application evaluated for use using photodynamic therapy as an antibacterial and crosslinking agent.

Synthesis and Characterization of Chitosan Polymer-Rose Bengal Nanoparticles:

Chitosan polymer-Rose Bengal nanoparticles were synthesized by conjugating spherical chitosan nanoparticles formed using an ionic gelation method with Rose Bengal using the procedure illustrated in FIG. 1 and described below. Chitosan purchased from Sigma-Aldrich, St. Louis, USA, was dissolved in 1 v/v % acetic acid solution at a concentration of 0.12 w/v %, and the pH was raised to 5 with 1M NaOH. Chitosan nanoparticles were formed spontaneously using an ionic gelation method by adding 0.1% sodium tripolyphosphate in water to chitosan solution in a ratio of 3:1 under stirring at a speed of 1000 rpm for 5 minutes.

Chitosan polymer-Rose Bengal nanoparticles were thereafter synthesized using chemical crosslinker carbodiimides (N-ethyl-N(3-dimethyl aminopropyl) carbodiimide—EDC). EDC (5 mM) 380 mg/400 mL and NHS 5 mM (230 mg/400 mL) was added followed by Rose Bengal (to get a ratio of 10:1 with chitosan). The conjugation reaction was carried out in the dark. The chitosan polymer-Rose Bengal nanoparticles formed were collected using centrifugation at 15,000 rpm for 20 minutes. The chitosan polymer-Rose Bengal nanoparticles were then dialyzed against an acetic acid buffer (pH 5.5) using a dialysis membrane (Sigma, cellulose tubing, cut off 1200014000 g/mol). The water was changed daily and dialysis was carried out for a period of 1 week. The dialysis was stopped when no Rose Bengal residues were detected in the UV-visible spectrum of the dialysate.

The chitosan polymer-Rose Bengal nanoparticle filtrate was next freeze-dried starting at −80° C. The chitosan polymer-Rose Bengal was formed as a dried cotton mass that was milled using a sterile glass stirrer to obtain a fine powder of nanoparticles. The nanoparticles were stored in a cool and dark place until further use.

Figure 8A:
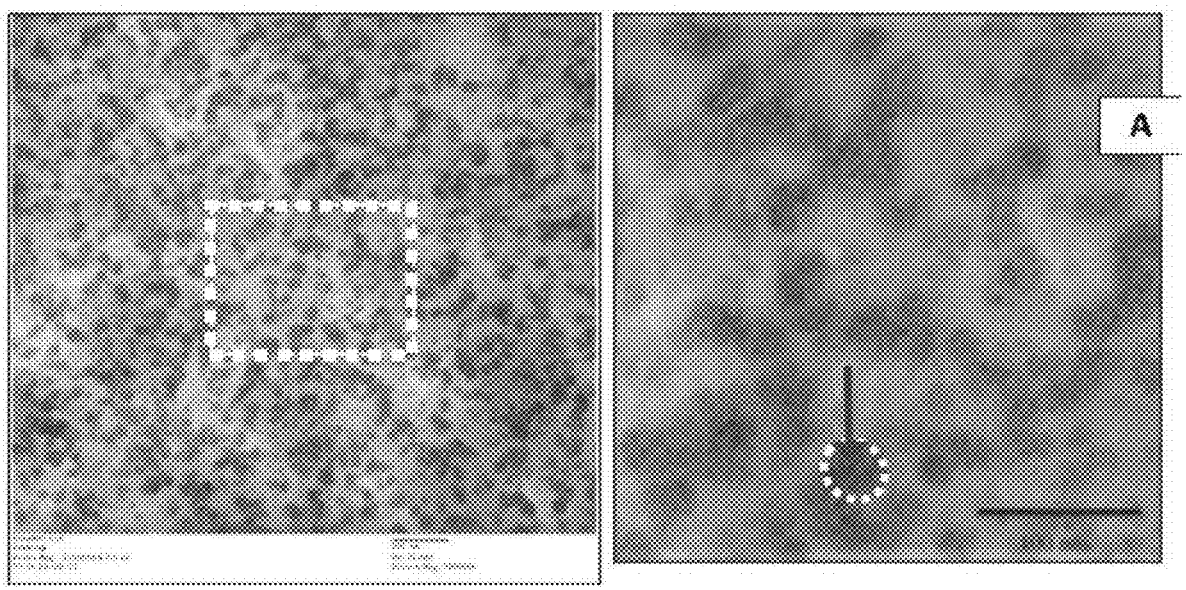
FIG. 8A shows a transmission electron microscopy image of chitosan polymer-Rose Bengal nanoparticles with the inset showing enlarged view (scale bar=100 nm). The chitosan polymer-Rose Bengal nanoparticles were of 60±20 nm in size.
Figure 8B:
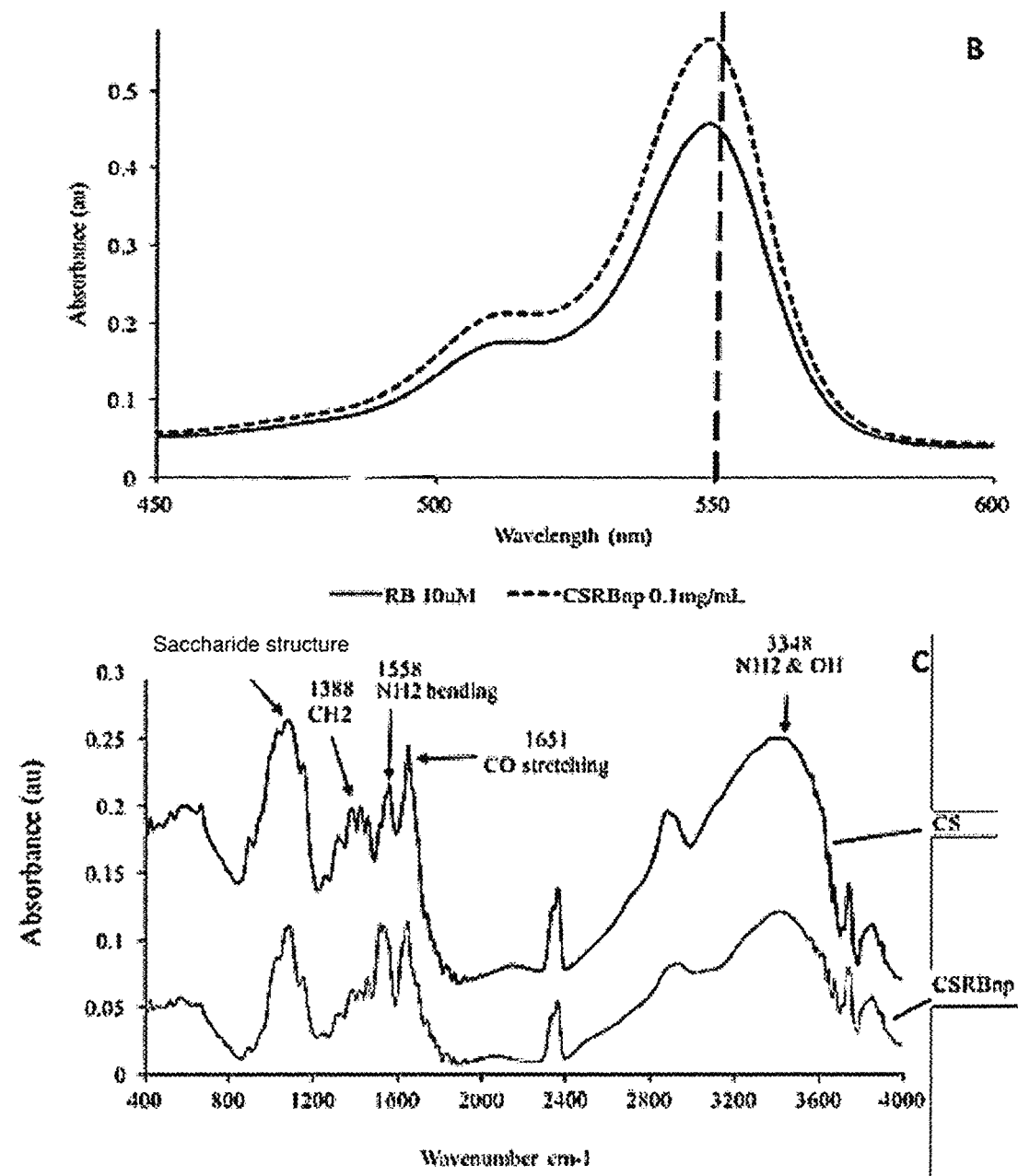
FIG. 8B shows a typical graph showing absorption spectrum of Rose Bengal and chitosan polymer-Rose Bengal nanoparticles. The absorption peak at 550 nm was not affected following conjugation of chitosan with Rose Bengal. (C) FTIR spectra of chitosan and chitosan polymer-Rose Bengal (400-4000 $cm^{-1}$ wavenumber). The amide peaks and presence of saccharide peak confirmed the conjugation of chitosan with Rose Bengal.

Absorption spectra for conjugated (chitosan polymer-Rose Bengal nanoparticles) and unconjugated (Rose Bengal) solutions were recorded using a UV-Visible spectrophotometer (Shimadzu 110e, Japan) (FIG. 8B). Photophysical characterization of chitosan polymer-Rose Bengal nanoparticles to determine the ratio of monomer to dimer (absorbance at 560 nm to 528 nm) at different concentrations was also carried out. The effective concentration of chitosan polymer-Rose Bengal nanoparticles was determined based on the highest monomer:dimer ratio (least aggregation). The conjugated chitosan polymer-Rose Bengal nanoparticles were analyzed for their chemical composition using Fourier Transform Infrared (FTIR) spectrophotometer (Shimadzu, Japan) (FIG. 8C). The prepared chitosan polymer-Rose Bengal nanoparticles were mixed with potassium bromide (1:100 w/w) for the FTIR spectroscopy (16 $cm^{-1}$ resolution, 32 scans per sample).

Figure 9:
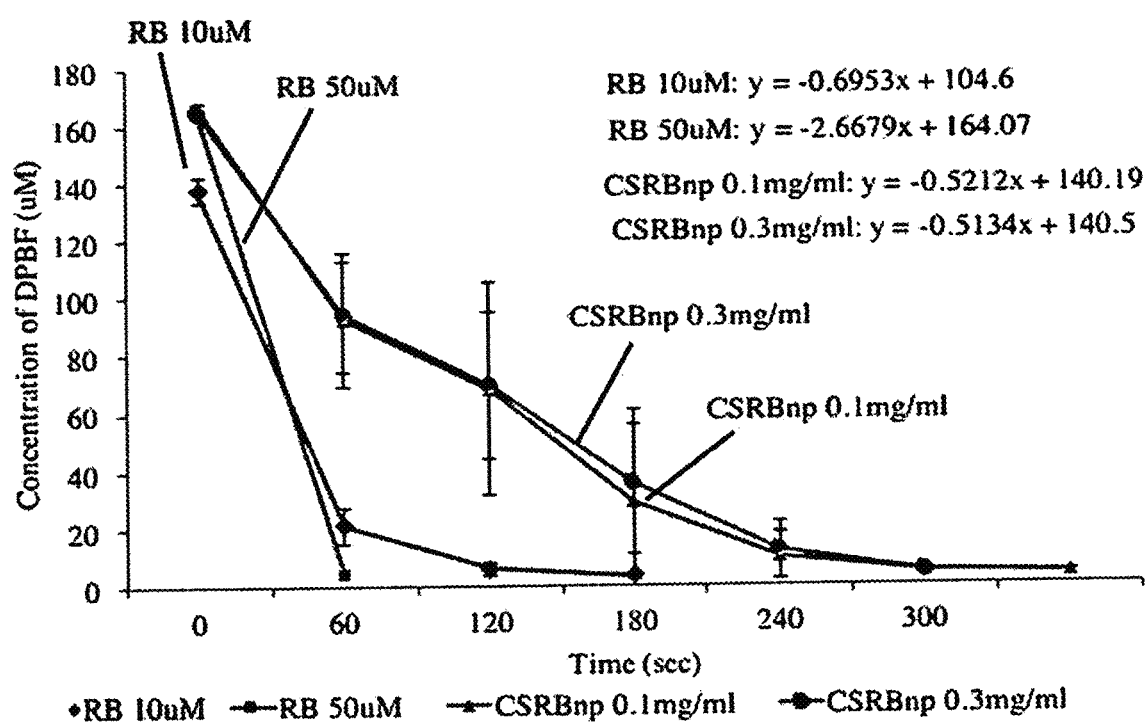
FIG. 9 shows graphically the oxidation of DPBF due to singlet oxygen generation following photoactivation of Rose Bengal and chitosan polymer-Rose Bengal nanoparticles measured as the reduction of DPBF absorbance.

Photo-oxidative characterization was conducted to assess the ability to generate singlet oxygen by the chitosan polymer-Rose Bengal nanoparticles. Measurements were carried out in a 24 well plate according to a procedure described in Hadjur et al., *J. Photochem. Photobiol., B;* 45, 170-178, 1998. Generation of singlet oxygen on photoactivation of Rose Bengal and chitosan polymer-Rose Bengal nanoparticles was studied photometrically using 1,3-diphenylisobenzofuran (DPBF), a singlet oxygen scavenger. 2 mL DPBF (200 μM in ethanol) was added (corresponding to absorbance intensity between 1.5 and 2 at 410 nm, in a 24 well plate) to 100 μL of different photosensitizer solutions (total volume=2.1 mL). Lumacare™ white light system with 540 nm (output power=50 mW) fiber was used as a light source. The decrease in absorbance intensity at 410 nm was monitored as a function of time using a UVVISIBLE™ microplate reader (Epoch, Biotek, USA). The rate of singlet oxygen production was related to the rate of decrease of DPBF absorbance at 410 nm as a function of irradiation time (FIG. 9).

Chemically Modified Phosphorylated Micro/Nano-Chitosan (P-NC) to Induce Biomineralization:

Biomimetic mineralization is a process carried out to imitate the natural process of mineralization, and thereby render the collage matrix of demineralized dentin remineralizable. The advantage of biomimetic mineralization is that it simulates the natural process of mineral crystal formation on the surface of organic or inorganic matrix without the need for harsh chemicals. The behavior of phosphorylated Non-Collagenous Proteins (NCPs) in biomineralization, suggest their suitability in methods for biomimetic mineralization to facilitate remineralization of demineralized connective and hard tissues such as dentin.

Figure 4:
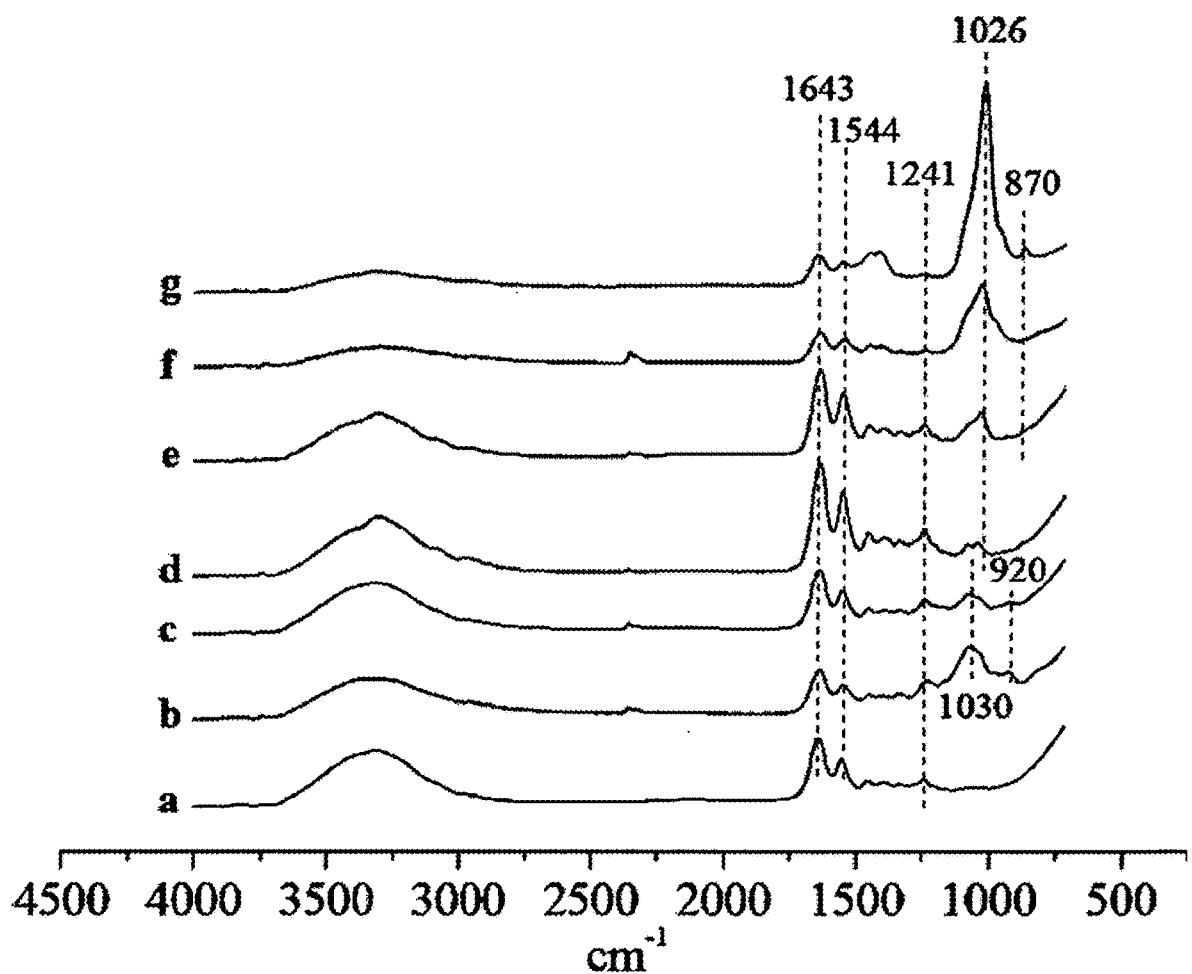
FIG. 4 shows graphically ATR-FTIR analysis of dentin surface: (a), the control sample; (b) specimen coated with phosphorylated chitosan, (c) specimen crosslinked with phosphorylated chitosan (d) specimen coated with phosphorylated chitosan after remineralization using non-fluoridated remineralizing solution; (e) untreated specimen after remineralization using fluoridated remineralizing solution; (f) specimen crosslinked with phosphorylated chitosan after remineralization using non-fluoridated solution; (g) sound dentin specimen with smear layer.
Figure 5:
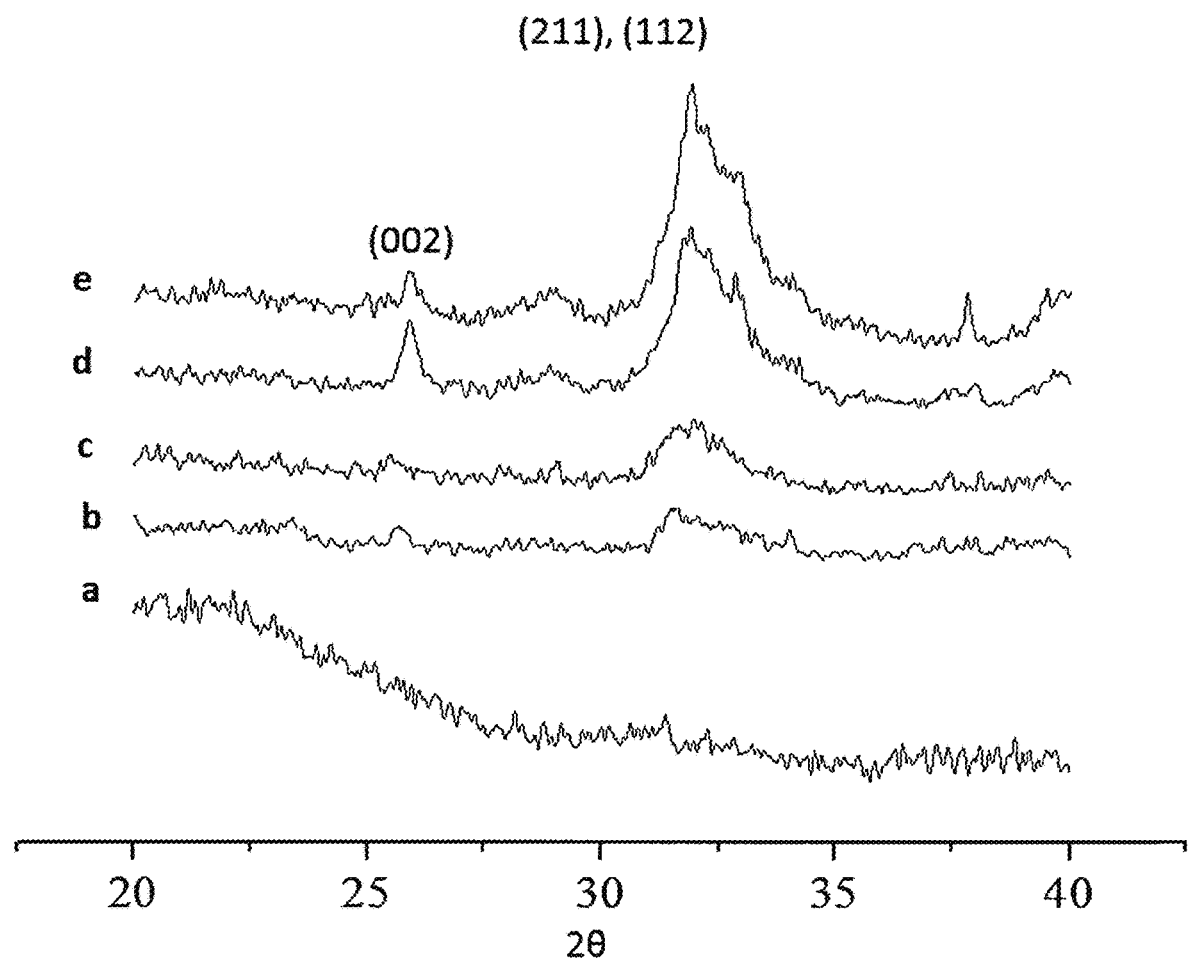
FIG. 5 shows graphically XRD diffraction of the surface of dentin specimen: (a), the control specimen; (b) specimen coated with phosphorylated chitosan after remineralization using non-fluoridated remineralization solution; (c) untreated specimen after remineralization using fluoridated remineralization solution; (d) specimen cross-linked with phosphorylated chitosan after remineralization using non-fluoridated remineralizing solution, (e) sound dentin specimen with smear layer.
Figure 6:
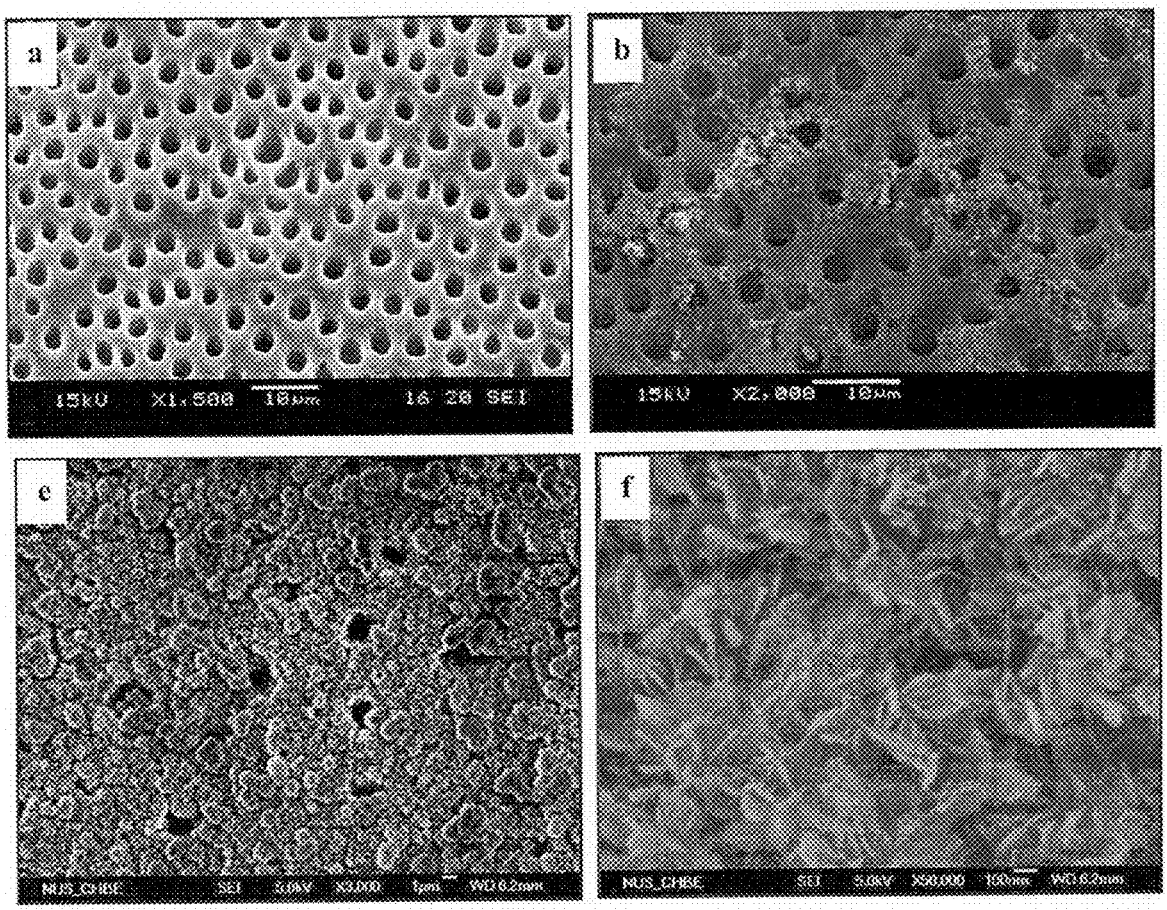
FIG. 6 shows SEM results of remineralization of partially demineralized dentin collagen (a) control sample; (b) sample coated with phosphorylated chitosan after remineralization using non-fluoridated remineralization solution (e) sample cross-linked with P-chi after remineralization using non-fluoridated remineralization solution; (f) highly magnified image of (e) showing petal-like mineral crystals.

In one embodiment, the collagen matrix of demineralized dentin is made to work as a scaffold for remineralization. Nanoparticles of phosphorylated chitosan P-chi of between about 40 nm to 80 nm were prepared using commercially available chitosan (Sigma, Chemical Co. USA) with low molecular weight (75-85% deacetylated) by the reaction of chitosan with phosphorous pentoxide, following the method developed by Nishi et al. Ibusuki S, Halbesma G J, Randolph M A, Redmond R W, Kochevar I E, Gill T J. Photochemically cross-linked collagen gels as three-dimensional scaffolds for tissue engineering. Tissue Eng. 2007 August; 13(8):1995-2001. Experiments were performed on micro sized particles of chitosan (not nanoparticles) to test the mechanism. The mechanism of the reaction is shown in FIG. 4, where the hydroxyl group is phosphorylated and the amino group is retained. Since the phosphorylated chitosan (P-chi) is water-soluble at pH 7.0, an aqueous solution of P-chi was prepared for treating dentin samples.

To coat P-chi on the surface of the dentin section/dentin collagen, 50 mg dentin collagen were mixed with 5 mL of P-chi solution (5 mg/mL) and then dried in a chemical hood until the water was completely vaporized. The covalent immobilization of P-chi on the surface of the dentin sections or dentin collagen particles was carried out by putting one dentin section or 50 mg dentin collagen particles to 10 ml P-chi solution containing glutaraldehyde (GA), which is a cross-linker (Sigma, Chemical Co. USA) of 0.25% (wt %) at 4° C. for 24 h. It was found that the phosphorylated chitosan when treated with demineralized dentin promoted biomineralization (FIGS. 2 to 6). The use of the composition for remineralizing the demineralized dentin advantageously aids not only reinforcement mechanically and chemically of the hard tissue, but also aids in promoting biomineralization of the interface subsequent to interfacial failure and penetration of saliva.

Evaluation of Cytotoxicity of Chitosan Polymer-Rose Bengal Nanoparticles:

To evaluate cytotoxicity approximately $1 \times 10^5$ NIH 3T3 mouse fibroblast cells (American Type Culture Collection CCL 1, Rockville, Md.) were seeded into 24 well plates in Dulbecco's Modified Eagle medium (DMEM) supplemented with 10% Bovine Serum and antibiotics and incubated for 48 hrs in 5% $CO_2$ incubator (Thermo Electron Corporation, USA). After incubation, chitosan polymer-Rose Bengal nanoparticles and Rose Bengal dissolved in DMEM were added into the cells and incubated for 15 min in dark. The cells were irradiated with a white light source and a 540 nm fiber (Lumacare Inc) for a total dose of 20 $J/cm^2$. Rose Bengal and chitosan polymer-Rose Bengal nanoparticles were also tested without irradiation. The cells were left in the media for 24 hours under incubation.

The supernatant media was removed without disturbing the cell line, and the cell layer was washed with 1 mL of phosphate-buffered saline. Cell survival was determined by the standard 3-(4, 5-dimethylthiazol-2-yl)-2, 5-diphenyltetrazolium bromide (MTT) assay (Sigma Aldrich) that determines the mitochondrial activity [34]. MTT medium was applied at a concentration of 0.5 mg % in phosphate-buffered saline and incubated for 4 hours. After the incubation period, MTT medium was removed, and 1 mL dimethyl sulfoxide was added to dissolve the insoluble formazan crystals. The absorbance at 540 nm was measured photometrically by using a UV-visible spectrophotometer (Epoch, Biotek, USA). Percentage survival was calculated based on control sample without any treatment as 100%. All analyses were repeated three times in triplicate, and the statistical significance was analyzed by one-way analysis of variance.

Uptake of Rose Bengal, MB and Chitosan Polymer-Rose Bengal Nanoparticles by *E. faecalis* Biofilm:

The uptake of Rose Bengal, methylene blue and chitosan polymer-Rose Bengal nanoparticles was evaluated on biofilm forms of *E. faecalis*. A seven day old biofilm of *E. faecalis* (ATCC 29212) was grown in 24 multi-well plates. 1 mL of overnight *E. faecalis* culture was added into each well of the multi-well plates and incubated at 37° C., 100 rpm. Fresh media was replenished every 48 hours to provide a constant supply of nutrients and to remove dead bacterial cells. On the eighth day, the media was removed from the wells, and the biofilm was carefully washed once with sterile deionized-water. Different concentrations of chitosan polymer-Rose Bengal nanoparticles (0.3, 0.5 & 1 mg/mL) and MB and Rose Bengal (10, 25, 50 & 100 µM) were added to the biofilm and incubated at 37° C. for 15 min, protected from ambient light. Three samples were used for each concentration. Excess photosensitizer solutions were removed leaving behind the bound Rose Bengal, MB and chitosan polymer-Rose Bengal nanoparticles in biofilm and washed once. The biofilm bacteria were treated with 1 mL of 2% SDS for 20 h in order to extract the cell-bound photosensitizers. The biofilms were disrupted and collected in eppendorf tubes. The biofilm bacteria were centrifuged (3000 rpm, 10 min) and the supernatant solution was taken for photosensitizer quantification. Quantification of photosensitizer was done spectrophotometrically (Epoch, Biotek, USA) at the absorption maxima of the Rose Bengal (540 nm). Calibration curves were constructed for each Rose Bengal in 2% SDS. Uptake values were obtained as the total Rose Bengal and MB concentrations (µM) extracted from both the 1 mL of planktonic and biofilm bacteria.

Effect of Rose Bengal and Chitosan Polymer-Rose Bengal Nanoparticles on the Membrane Integrity of Planktonic Bacteria:

Leakage of cytoplasmic contents (DNA) is a characteristic indication of damage to the bacterial cytoplasmic membrane. Absorbance at 260 nm was used to estimate the amount of intracellular contents leaked from bacteria subjected to different photosensitizers and photodynamic therapy. *E. faecalis* (ATCC 29212) was incubated overnight at 37° C. under agitation in the Brain-Heart Infusion (BHI) medium (Sigma, USA). The culture was centrifuged (4000 rpm, 10 min, 4° C.), supernatants discarded and washed twice in sterile deionized water (DIW). The cells were resuspended in deionized water and adjusted to $10^7$ CFU/mL (optical density 0.7) at 600 nm. The cell suspension (1 mL) was then added into eppendorf tubes and centrifuged. The supernatants were discarded and the cell pellets were treated with different photosensitizer solutions and maintained at 37° C. for 15 min, protected from ambient light. The kinetics of release of intracellular contents, treated bacterial cells were filtered (0.2 µm pore size, Pall) and absorbance of the filtrate recorded at 260 nm ($OD_{260}$). For photodynamic therapy, the photosensitized cells were centrifuged and cell pellets irradiated (5 $J/cm^2$, 540 nm). The % change in OD260 at 15 min post sensitization and after irradiation with 5 $J/cm^2$ was calculated with respect to the OD260 of the sample measured at 0 min.

Assessment of Antibacterial Efficacy of Rose Bengal and Chitosan Polymer-Rose Bengal Nanoparticles:

*E. faecalis* (ATCC 29212) was used to test the antibacterial efficacy of Rose Bengal and chitosan polymer-Rose Bengal nanoparticles in both planktonic and biofilm forms. Planktonic cell pellets ($10^9$ cells/mL) were obtained and the cell pellets treated with 1 mL of Rose Bengal (10 µM) and chitosan polymer-Rose Bengal nanoparticles (0.1 & 0.3 mg/mL), at 37° C. for 15 min, in the manner previously described and protected from ambient light to allow sensitization. Dark toxicity was evaluated after 15 min of sensitization with the two treatment solutions. In the case of photodynamic therapy, the photosensitizer solutions were removed leaving a thin smear at the bottom of the eppendorf tubes. The sensitized planktonic-bacteria were irradiated using a 540 nm fiber with doses of 2 and 5 $J/cm^2$. After treatment, cell pellets were resuspended in sterile deionized-water (1 mL) and 100 µL of the suspension was plated in freshly poured BHI agar plates after serial dilution. Colonies were counted after 24 hours of incubation at 37° C. and expressed as log colony forming units (CFU) per mL.

In order to test the antibacterial-efficacy of nanoparticulates on bacterial-biofilm, 7-days old biofilm of *E. faecalis* (ATCC 29212) was grown in well of multiwell-plates as mentioned above. On the eighth day, the media was removed from the wells, and the biofilm was carefully washed once with sterile deionized-water. The biofilm-bacteria was treated with chitosan polymer-Rose Bengal nanoparticles and Rose Bengal and exposed to photodynamic therapy with different doses. Sensitization was done using 1 mL of Rose Bengal (10 µM) and chitosan polymer-Rose Bengal nanoparticles (0.1 & 0.3 mg/mL) at 37° C. for 15 min, protected from ambient light. Subsequently, the excess photosensitizer solutions were removed leaving behind the bound chitosan polymer-Rose Bengal nanoparticles and Rose Bengal. Dark toxicity was evaluated after sensitization period with the two treatment solutions. In case of photodynamic therapy, the sensitized biofilm-bacteria were irradiated using a 540 nm fiber with dosage of 20, 40 and 60 $J/cm^2$; and fractionated dosage of 10 and 20 $J/cm^2$ twice. After treatment, the biofilms were washed gently and 1 mL of sterile deionized-water was added. Biofilmbacteria were disrupted mechanically and plated in freshly poured BHI agar plates following serial dilutions. Control wells were maintained in sterile deionized-water. Colonies were counted after 24 hours of incubation at 37° C. and expressed as log colony forming units (CFU) per mL. The experiments were carried out in triplicates and the mean values were calculated.

Assessment of Biofilm-Structure Following Rose Bengal and Chitosan Polymer-Rose Bengal Nanoparticles Treatment:

The structure of the 7-days old biofilm following treatment with nanoparticulates was assessed using confocal-laser-scanning-microscopy (CLSM). *E. faecalis* (ATCC 29212) biofilm was grown on a glass bottom culture dishes. Following treatment with Rose Bengal (10 µM) and chitosan polymer-Rose Bengal nanoparticles (0.3 mg/mL) the as mentioned above, biofilms were washed with 1 mL of sterile deionized-water. The biofilms were then stained with 200 µL, of Live/Dead® Baclight™ stain (Molecular Probes, Eugene, Oreg.) and incubated in the dark for 10 minutes. The biofilm-structures were then viewed under spinning disk confocal-laser-scanning microscopy (Olympus, Japan). Kr/Ar laser was the source of illumination with 488 nm excitation and long-pass 500-523 nm and 622-722 nm emission filter settings for green and red signals respectively. Nine different areas were imaged from each sample using a 60× oil objective. The optical sections of the biofilm-structure were first recorded then subsequently analyzed using Velocity® software. Student t-test was used to compare the thickness of the biofilm before and after nanoparticulates treatment.

Figure 7:
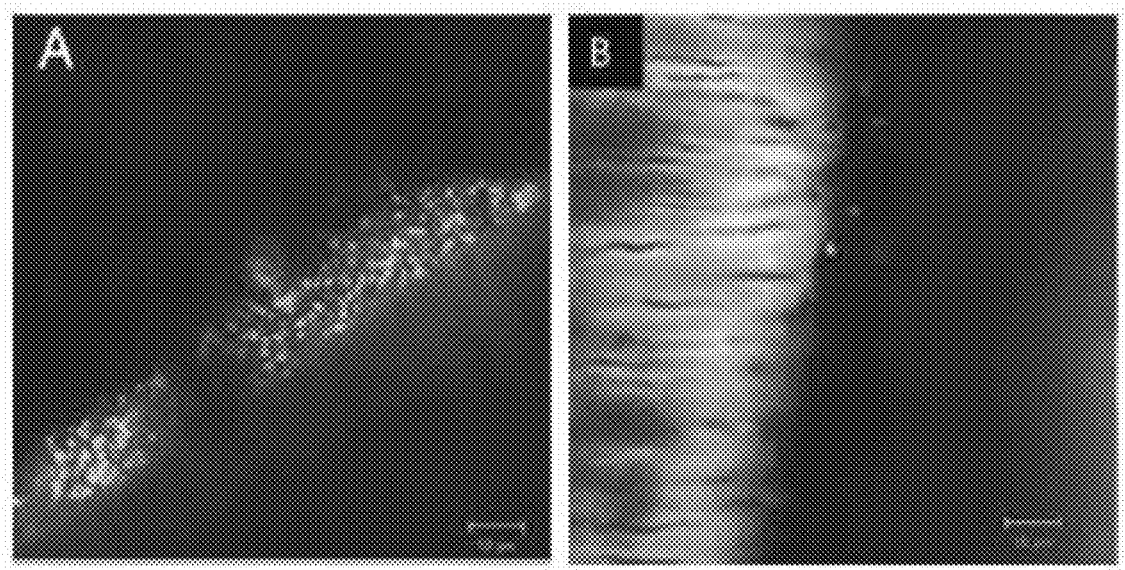
FIG. 7 shows confocal Laser Scanning Microscopy microscopic Images showing significant biofilm proliferation at the sealer-dentin interface in the control sample, and with no conspicuous biofilm proliferation at the sealer-dentin interface, where the dentin were conditioned with the phosphorylated chitosan nanoparticles.

Effects of Chitosan Nanoparticles and Dentin Surface Treatment with Conjugated Chitosan on Biofilm Formation within the Sealer-Root Dentin Interfaces:

Bacterial recolonization after treatment still remains a major concern in endodontically treated teeth. Chitosan and its variants are biocompatible natural biopolymers, which possess versatile biological activities including antibacterial properties. An assessment of biofilm formation within the sealer-dentin interfaces of roots filled with chitosan nanoparticles modified sealer and its combination with root dentin surface treatment by phosphorylated chitosan and/or photosensitizer conjugated chitosan (Rose Bengal-chitosan). Standardized specimens comprising of coronal 4 mm root segments of bovine incisors (n=17) were surface treated with the test materials and filled with gutta-percha rubber and zinc oxide eugenol (ZOE) sealer containing chitosan nanoparticles. The control group was filled with gutta-percha rubber and zinc oxide eugenol sealer. After setting at 100% relative humidity for 7 days, samples were conditioned at 37° C. for 4 weeks in simulated saliva solution. Monospecies biofilms of *Enterococcus faecalis* (ATCC 29212) were grown on the specimens for 7 days in a chemostat-based biofilm fermentor, mimicking pathogenic oral conditions. The extent of biofilm formation within the sealer dentin interface was assessed using confocal laser scanning microscopy and scanning electron microscopy. Biofilm surface area data was analyzed by Kruskal-Wallis and Mann-Whitney U tests. Specimens with chitosan nanoparticles in the sealer alone (489.77±269.66 µm$^2$) and those receiving phosphorylated chitosan and photosensitizer conjugated chitosan/phosphorylated chitosan surface treatment (574.1±186.21 µm$^2$, 949.3±510.03 µm$^2$, respectively) showed less biofilm formation than the zinc oxide eugenol sealer control group (2438.52±383.26 µm$^2$, p<0.05). Within the test model used, incorporating chitosan nanoparticles into zinc oxide eugenol sealer and the surface treatment with phosphorylated chitosan or Rose Bengal-chitosan/phosphorylated chitosan increased the resistance to biofilm formation. The results are illustrated in FIG. 7.

Photodynamic Crosslinking of Dentin-Collagen:

Sixteen freshly extracted human incisors and eight bovine incisors were stored in 0.9% saline until use. The bovine teeth were used for mechanical testing while the human teeth were used for chemical and enzymatic-degradation analysis. Dentin sections of 0.5 mm thickness were prepared from either side of the root canal lumen using a slow speed diamond wafering blade (Buehler, UK) under continuous water irrigation. The sections were further prepared into rectangular dimensions of 12×2×0.5 mm (human) and 16×2×0.2 mm (bovine) by grinding in wet emery paper of grit sizes 400, 800 and 1000 under continuous water irrigation. The dentin sections were demineralized in 1M EDTA (pH=7.4) for seven days. The resulting dentin collagen specimens were rinsed for 10 minutes in deionized water to remove residual EDTA and subsequently stored in sterile deionized-water at 4° C. The demineralized dentin collagen specimens (total—48) were randomly divided into four treatment groups (n=12): 1) No-treatment—(Control); 2) 2.5% glutaraldehyde; 3) Rose Bengal 10 µM; and 4) chitosan polymer-Rose Bengal nanoparticles 0.3 mg/mL chitosan polymer-Rose Bengal. The dentin-collagen samples were crosslinked with glutaraldehyde for a period of 6 hours. In photodynamic crosslinking, collagen-samples were placed in a 24 well-plate (area of 2 cm$^2$/well) and immersed in 1 mL of Rose Bengal or chitosan polymer-Rose Bengal nanoparticles solution for 15 min. After the sensitization period, excess Rose Bengal and chitosan polymer-Rose Bengal nanoparticles were removed and the photosensitized collagen was activated with a non-coherent light (540 nm, 20 J/cm$^2$) (LumaCare Inc., NewPort Beach, Calif., USA). Crosslinked specimens were thoroughly washed in deionized-water three times, stored in a vacuum dessicator overnight and then tested for chemical analysis. For the enzymatic degradation analysis, the specimens were lyophilized for 24 hours. The bovine dentin-collagen specimens were maintained in deionized-water to be used for mechanical testing.

Chemical Analysis:

The vacuum desiccated collagen specimens were treated with liquid nitrogen, ground and mixed with potassium bromide (1:100 w/w) for the fourier transform infrared (FTIR) spectroscopy (16 cm' resolution, 100 scans per sample) (Shimadzu, Kyoto, Japan).

Determination of Mechanical Properties:

Enzymatic degradation analysis was conducted to quantify the amino acid release using Ninhydrin assay as described by Mandl et al. Mandl, I., J. D. Maclennan, and E. L. Howes, *Isolation and characterization of proteinase and collagenase from Cl. histolyticum*. J Clin Invest, 1953. 32(12): p. 1323-9. The dentin-collagen specimens were subjected to enzymatic degradation using collagenase from *Clostridium histolyticum* with an activity of 125 CDU/mg solid (P/N C-0130; Sigma). Desiccated collagen specimens (5 mg) were added into 5 mL of buffer solution (50 mM HEPES containing 0.36 mM CaCl$_2$) and incubated at 37° C. for 30 min., 0.1 mL collagenase enzyme (0.1 mg/mL in HEPES buffer) was added into the collagen containing buffer solution and incubated at 37° C. in an orbital incubator (100 rpm). After 1, 2, 3 and 7 days of degradation, 200 µL. of the solution was added into ninhydrin reagent (2 mL), mixed well and kept in boiling water for 30 min. The containers were allowed to cool to room temperature and 10 mL of 50% isopropanol was added. The amount of free amino acids released following degradation of collagen specimens after heating with ninhydrin, was proportional to the optical absorbance (560 nm) of the solution. The amount of amino acids released from the crosslinked and non-crosslinked dentin-collagen specimens were quantified using the standard curve of L-Leucine.

Determination of Mechanical Properties:

The fully-hydrated bovine dentin collagen specimens from all four test groups were used for tensile testing (Instron 5544™, Instron Corporation, Canton, Mass.) with a 100 N load cell. The specimens were positioned in the loading jig by gripping the two ends (4 mm) and subjected to tensile load at a crosshead speed of 1 mm/min until failure occurred. Care was taken to keep the samples hydrated at all times during the test. The stress-strain curve per sample was plotted for all the groups. The ultimate tensile strength and toughness (MPa), represented by the area under the stress-strain curves were calculated using OriginPro 8.1™ software (OriginLab Corporation, MA).

TEM Evaluation:

Four specimens from each group were processed for TEM evaluation after crosslinking. The collagen specimens were fixed overnight in 2.5% glutaraldehyde (0.1M phosphate buffer). All specimens for the TEM were prepared following previous protocol [3]. The 90 nm thick sections were prepared along the cross-section of the specimens and examined under TEM (Hitachi H-7000, Tokyo) at 80 kV.

Characterization of Polymeric Photosensitizes Chitosan Polymer-Rose Bengal Nanoparticles:

FIG. 8A shows electro micrographs of the aggregates of spherical chitosan polymer-Rose Bengal nanoparticles under TEM with 60±20 nm size. The zeta potential of the chitosan polymer-Rose Bengal nanoparticles was found to be +30±0.8 mV. The absorption spectra obtained for chitosan polymer-Rose Bengal nanoparticles displayed bands characteristic of Rose Bengal is illustrated in FIG. 8B. The amount of Rose Bengal uptake by the conjugated chitosan polymer-Rose Bengal nanoparticles was calculated to be 14 $\mu$M per 0.1 mg. This confirms that Rose Bengal is attached to the chitosan polymer chain. FTIR spectra of conjugated chitosan Rose Bengal illustrated graphically in FIG. 8C showed bands that could be assigned to the amide bonds between chitosan and Rose Bengal. Two characteristic peaks at 1651 (amide I, carbonyl stretching vibration) and 1558 $cm^{-1}$ corresponding to ($NH_2$ bending) were prominent in chitosan and chitosan polymer-Rose Bengal spectra (Moczek & Nowakowska, 2007). However, the ratio of intensities at 1558 and 1652 $cm^{-1}$ was higher in chitosan polymer-Rose Bengal when compared to chitosan suggesting the reduction of amide I bonds due to utilization of free amine groups of chitosan to form bonds with CO— group of Rose Bengal. The peak (900-1100 $cm^{-1}$) corresponding to the saccharide group of chitosan was also prominent in the chitosan polymer-Rose Bengal.

Chitosan polymer-Rose Bengal nanoparticles showed the ability to produce singlet oxygen upon photoactivation similar to Rose Bengal (FIG. 9) observed as a decrease in the DPBF concentration. The singlet oxygen release was high enough to convert all the available DPBF for both the photosensitizer. The rate of singlet oxygen generation increased with increase in the concentration of both the photosensitizer used. Following results of the characterization of chitosan polymer-Rose Bengal nanoparticles, concentration of 0.3 mg/mL was used in all the subsequent experiments.

Figure 10:
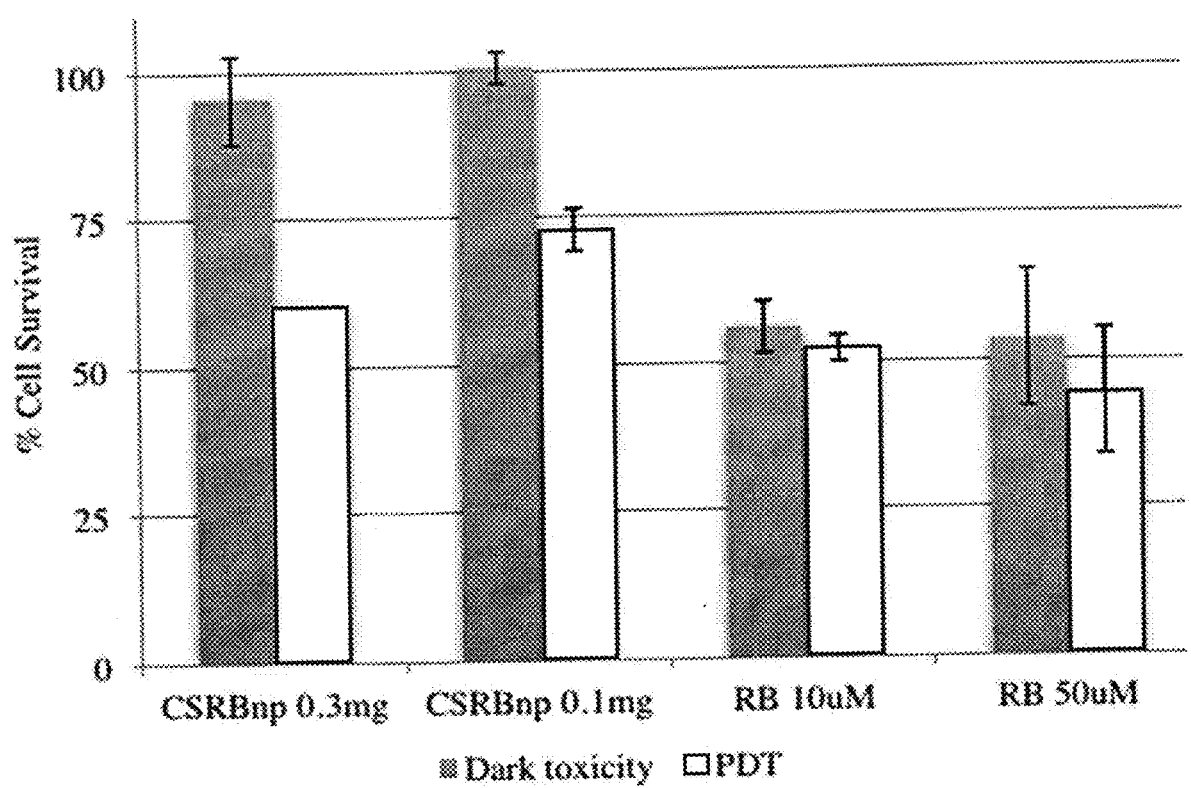
FIG. 10 shows a graph showing cell survival following treatment with Rose Bengal and chitosan Rose Bengal nanoparticles with and without photodynamic therapy. Photodynamic therapy resulted in significantly increased cytotoxicity as compared to chitosan Rose Bengal nanoparticles treatment without photodynamic therapy. ($p<0.05$)

Cytotoxicity Assay Using Rose Bengal and Chitosan Polymer-Rose Bengal Nanoparticles:

FIG. 10 shows the cell survival in percentage after different photosensitizer treatments. Chitosan polymer-Rose Bengal nanoparticles did not show any dark toxicity with 15 min exposure time. Following irradiation, toxicity increased up to 50% depending upon the chitosan polymer-Rose Bengal nanoparticles concentration used. Rose Bengal showed higher dark toxicity and further reduction of cell survival after photodynamic therapy.

Uptake of Rose Bengal, Methylene Blue and Chitosan Polymer-Rose Bengal Nanoparticles p by *E. faecalis* Biofilm:

Conjugation of anionic photosensitizer (Rose Bengal) with chitosan enhanced the uptake into the bacterial cells. The Rose Bengal alone showed minimal diffusion in contrast to chitosan polymer-Rose Bengal nanoparticles.

TABLE 1

Uptake from bacterial cells obtained after incubation with different photosensitizers.

| photosensitizer | Biofilm *E. faecalis* photosensitizer ($\mu$M) uptake/mL of cells |
|---|---|
| RB 10 $\mu$M | 2.72 ± 0.15 |
| RB 25 $\mu$M | 2.80 ± 0.09 |
| RB 50 $\mu$M | 3.01 ± 0.11 |
| RB 100 $\mu$M | 3.68 ± 0.17 |
| MB 10 $\mu$M | 0.96 ± 0.07 |
| MB 25 $\mu$M | 1.75 ± 0.21 |
| MB 50 $\mu$M | 3.15 ± 0.16 |
| MB 100 $\mu$M | 5.07 ± 0.19 |
| CSRBnp 0.3 mg/mL | 16.15 ± 5.82 |
| CSRBnp 0.5 mg/mL | 24.06 ± 9.77 |
| CSRBnp 1.0 mg/mL | 40.68 ± 4.32 |

Values represent the uptake in $\mu$M/mL of cells obtained after incubation of biofilm bacteria with Rose Bengal, methylene blue (MB) and chitosan polymer-Rose Bengal nanoparticles. Values are the means of three readings±standard deviations. There was a significant increase in uptake of photosensitizer by bacterial cells when conjugated with chitosan. Biofilm showed significant increase in uptake of chitosan polymer-Rose Bengal nanoparticles as compared to planktonic bacteria. (P<0.05).

The exact quantity of Rose Bengal uptake was calculated using the standard curve of Rose Bengal in 2% SDS. Chitosan nanoparticles are known to kill bacteria by inducing membrane permeability and subsequent leakage of intracellular components (Rabea et al. 2003). In addition, chitosan polymer-Rose Bengal nanoparticles were also found to be positively charged and therefore more amenable to permeation. The short exposure time to chitosan polymer-Rose Bengal nanoparticles may therefore operate to enhance entry of the Rose Bengal into the cells through the pores created by the chitosan nanoparticles.

Figure 11:
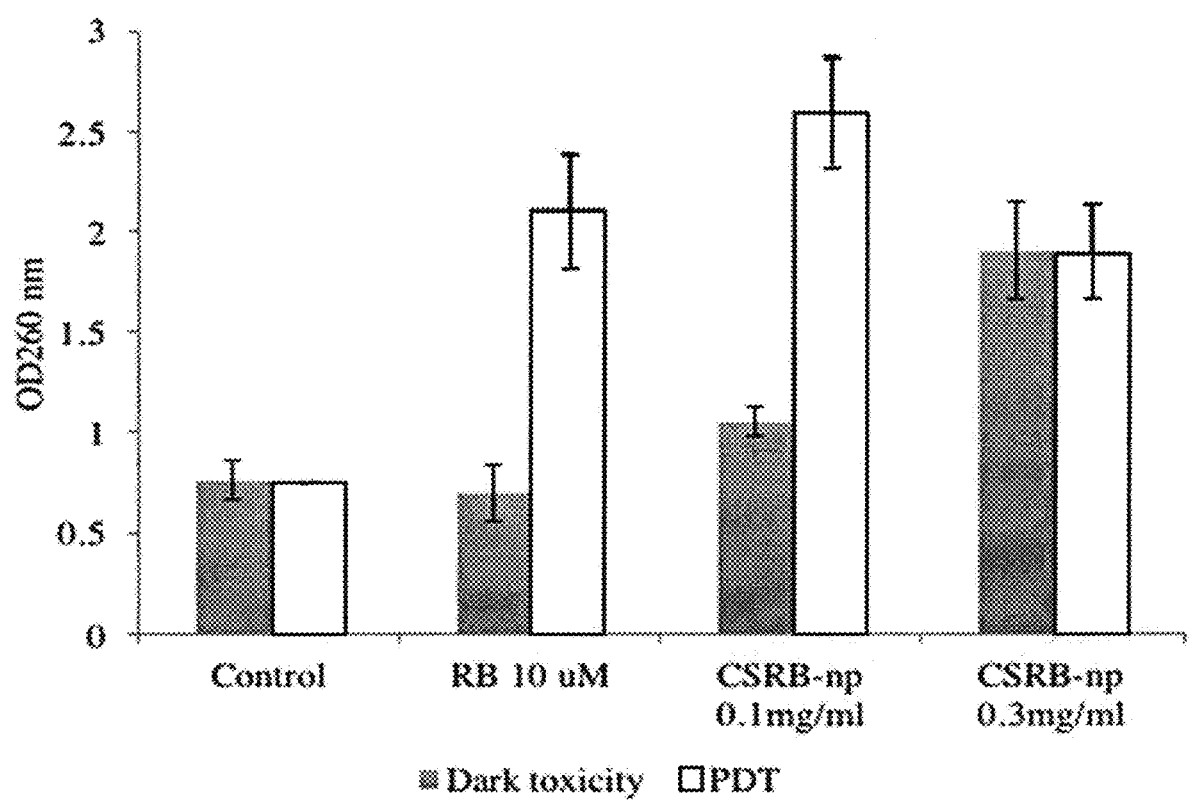
FIG. 11 illustrates a graph showing the release of cell constituents (absorbance at 260 nm) following treatment with Rose Bengal and chitosan Rose Bengal nanoparticles with and without photodynamic therapy. Chitosan polymer-Rose Bengal nanoparticles at higher concentration showed inherent ability to induce bacterial membrane damage.

Effect of Rose Bengal and Chitosan Polymer-Rose Bengal Nanoparticles on the Membrane Integrity of Planktonic Bacteria:

Bacterial membrane damage and subsequent leakage of cell constituents were higher with chitosan polymer-Rose Bengal nanoparticles than Rose Bengal without photodynamic therapy as for example is illustrated graphically in FIG. 11. Following photodynamic therapy both Rose Bengal and chitosan polymer-Rose Bengal nanoparticles showed increased absorbance at 260 nm. Chitosan polymer-Rose Bengal nanoparticles at 0.3 mg/mL showed inherently higher ability to induce bacterial membrane damage as compared to lower concentration used.

Figure 12:
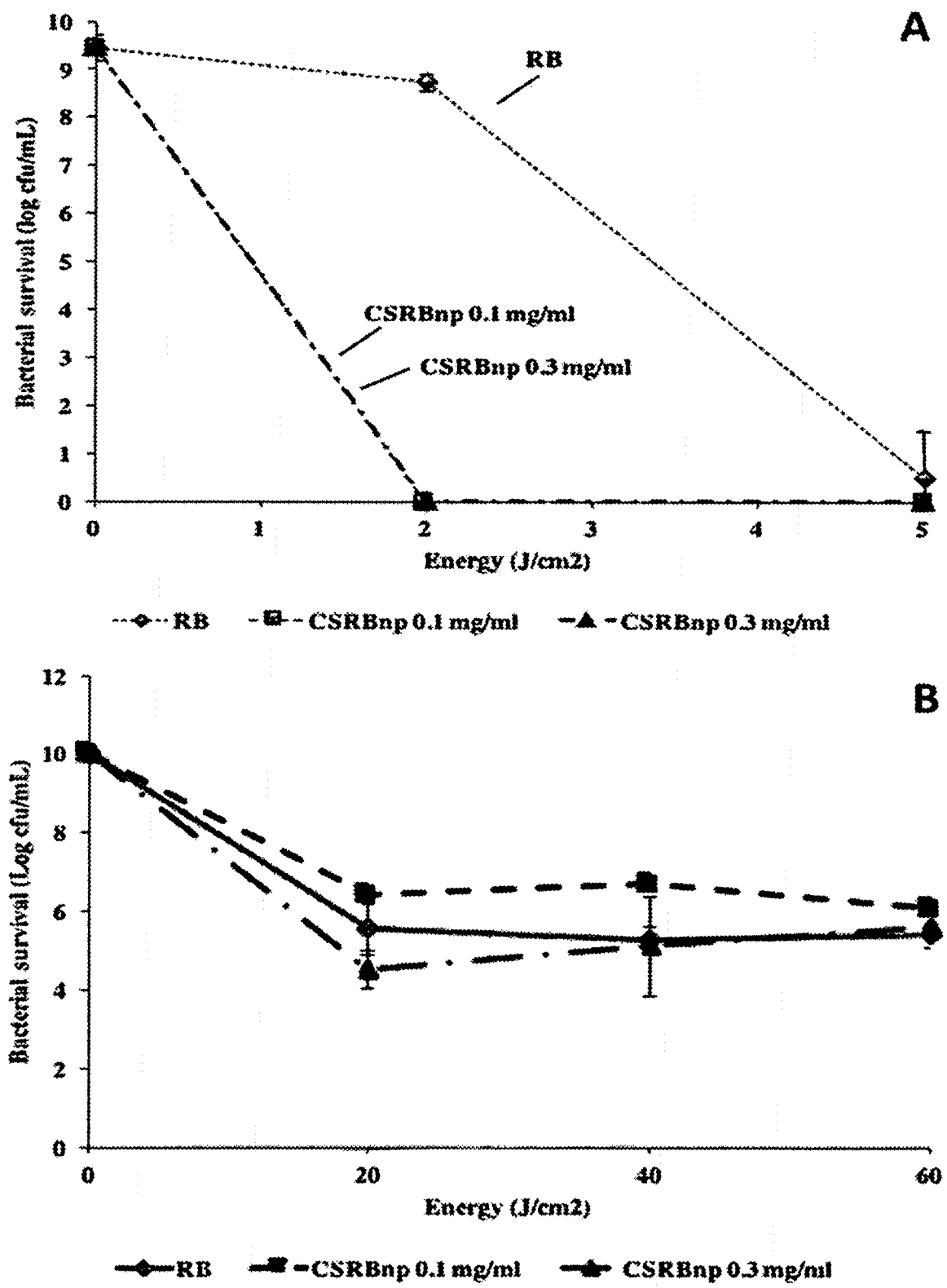
FIG. 12 shows graphically log number of E. faecalis in planktonic (A) and biofilm (B & C) forms surviving the photodynamic therapy conducted in a multiwell plate. There was a significant difference in the killing by chitosan polymer-Rose Bengal nanoparticles compared to Rose Bengal. Error bars show the standard deviation from average value.
Figure 12:
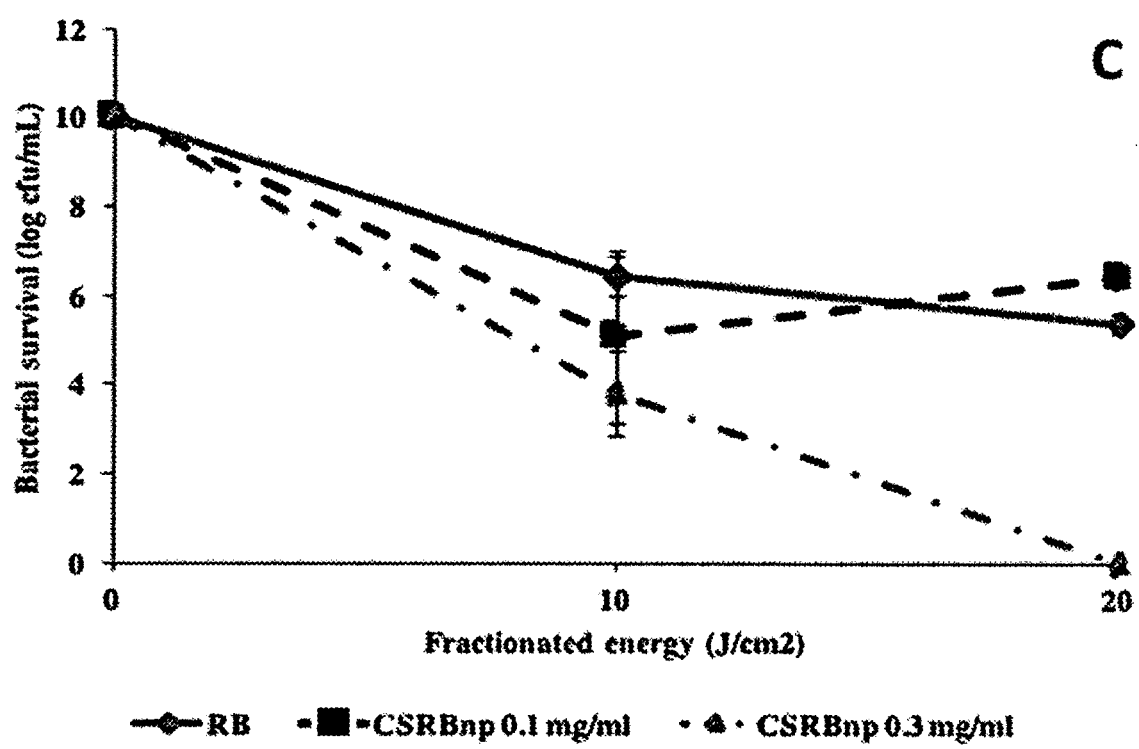

Assessment of Antibacterial Efficacy of Rose Bengal and Chitosan Polymer-Rose Bengal Nanoparticles:

FIG. 12 shows the antibacterial efficacy of Rose Bengal and chitosan polymer-Rose Bengal nanoparticles on planktonic and biofilm-bacteria. Chitosan polymer-Rose Bengal nanoparticles showed almost complete killing of planktonic *E. faecalis* even after 15 min of sensitization. In test studies, chitosan polymer-Rose Bengal nanoparticles and Rose Bengal showed complete planktonic bacterial killing at 2 and 5 J/cm² respectively see FIG. 12, slide (A). In case of biofilm-bacteria, both chitosan polymer-Rose Bengal nanoparticles and Rose Bengal did not show complete killing even at 60 J/cm² (FIG. 12, slide B). Following fractionation of the photodynamic therapy, complete elimination of biofilm bacteria was obtained with chitosan polymer-Rose Bengal nanoparticles (0.3 mg/mL) and not with Rose Bengal (FIG. 12, slide C). Fractionation of light dosage during PDT enhances the availability of molecular oxygen by providing a lag phase to allow oxygen replenishment. Likewise the slower release of singlet oxygen as observed with CSRBnp could provide sufficient time for molecular oxygen to be replenished in the site of PDT and prolong the antibacterial effect. This can also promote deeper penetration of singlet oxygen into the biofilm structure thus, resulting in complete biofilm elimination.

Figure 13:
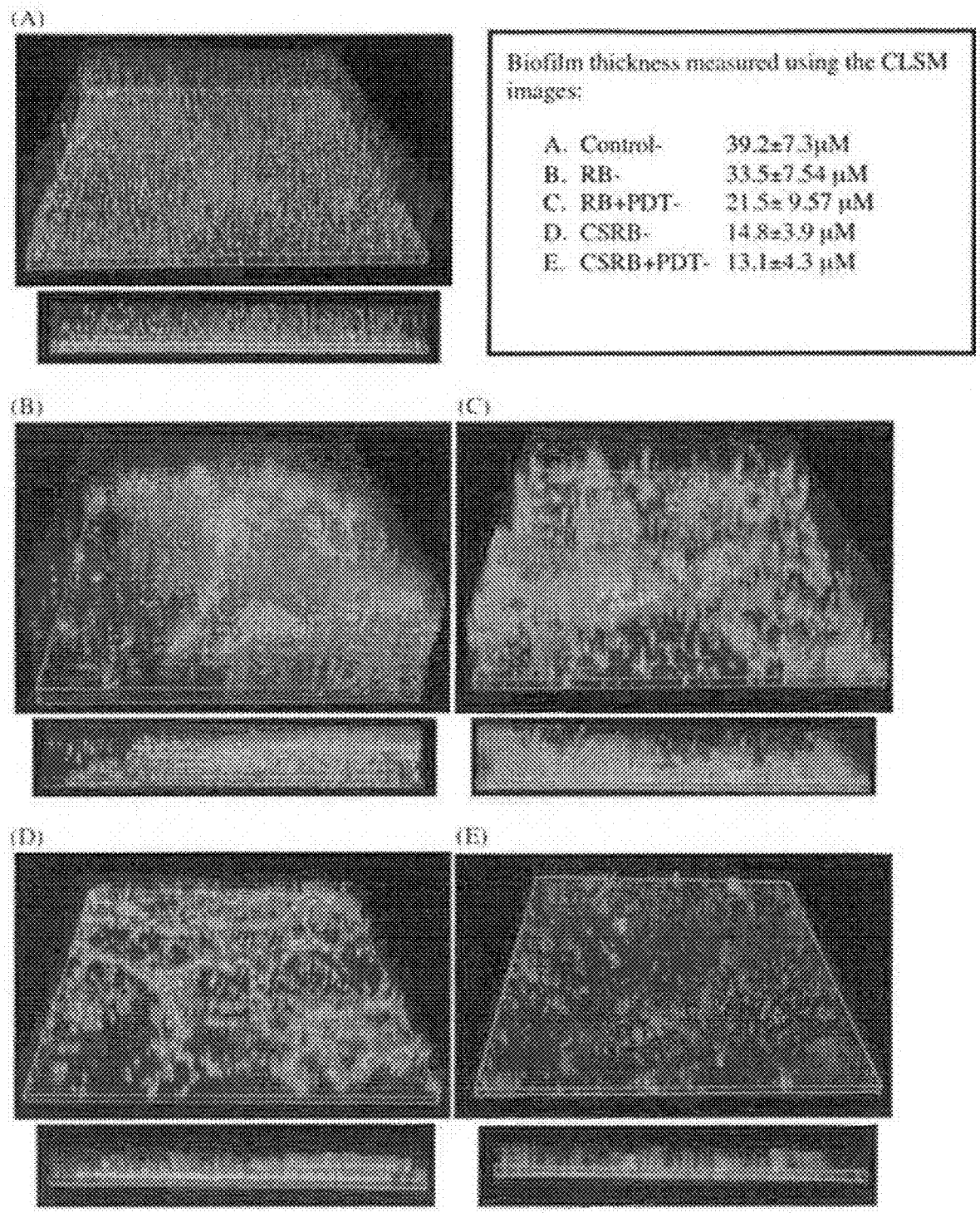
FIG. 13 shows three-dimensional confocal laser scanning microscopy reconstruction of the E. faecalis biofilm subjected to photodynamic therapy using Rose Bengal and chitosan polymer-Rose Bengal nanoparticles. (Inlet shows the sagittal section) (60×). (A) The biofilm receiving no treatment, (B) the biofilm subjected to sensitization with Rose Bengal, (C) the biofilm subjected to sensitization with Rose Bengal followed by irradiation (40 $J/cm^2$), (E) the biofilm subjected to sensitization with chitosan polymer-Rose Bengal nanoparticles, and (F) the biofilm subjected to chitosan polymer-Rose Bengal nanoparticles and irradiation (40 $J/cm^2$)

Assessment of Biofilm-Structure Following Rose Bengal and Chitosan Polymer-Rose Bengal Nanoparticles Treatment:

FIG. 13 shows CLSM images (A) to (E) of the bacterial-biofilms before and after photodynamic therapy treatment. In the untreated control, the biofilm-structure consisted of both live (green) and dead (red) bacterial-cells in a multi-layered architecture. The number of live bacterial-cells was observed to be higher as compared to the dead cells. The thickness of biofilm-structure was found to be variable at different locations (39.2±7.3 µM). Both the dark toxicity and photodynamic therapy treatment groups with Rose Bengal and chitosan polymer-Rose Bengal nanoparticles showed reduction in the biofilm thickness and biofilm-architecture was altered in case of chitosan polymer-Rose Bengal nanoparticles. Rose Bengal showed lower killing efficacy due to dark toxicity alone and irradiation resulted in higher killing of biofilm bacteria. However, the biofilm architecture was not disrupted. Distribution of viable bacteria reduced significantly and the multilayered structure as observed in the control biofilm was disrupted following chitosan polymer-Rose Bengal nanoparticles treatment. Bacterial-biofilms exposed to chitosan polymer-Rose Bengal nanoparticles were completely disrupted with conspicuous loss of the intricate three-dimensional form after PD treatment. The thickness of the biofilm reduced significantly to 13.1±4.3 µM ($p<0.01$) and 21.5±9.57 µM ($p<0.05$) after PD treatment with chitosan polymer-Rose Bengal nanoparticles and Rose Bengal respectively.

Figure 14:
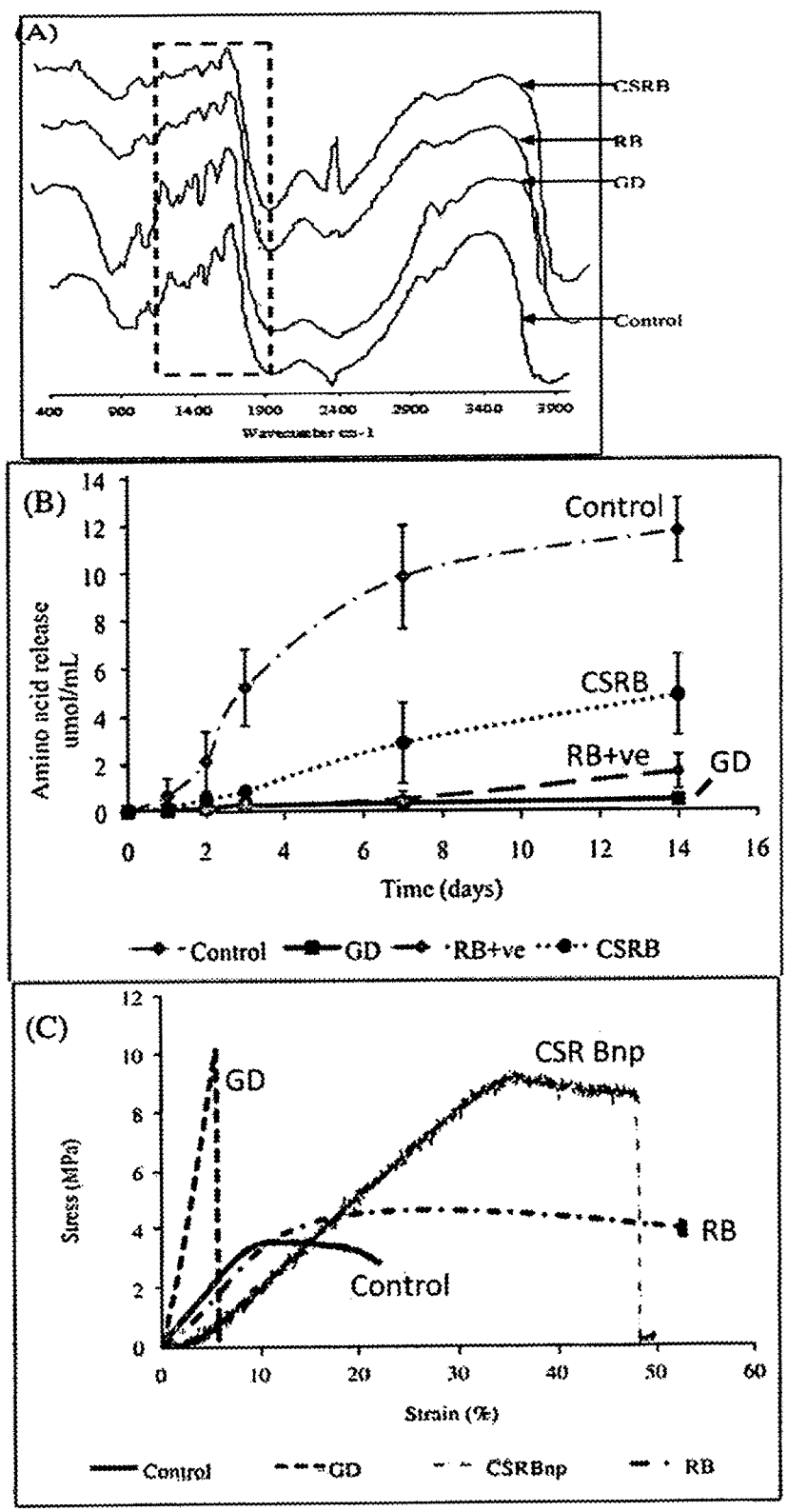
FIG. 14 shows schematically FTIR spectra of dentin-collagen (A); enzymatic degradation of dentin-collagen (B); and stress-strain curve after mechanical testing of dentin-collagen following crosslinking (C)

Photodynamic Crosslinking of Dentin-Collagen:

FIG. 14A shows schematically the FTIR spectra obtained from dentin-collagen. The amide I bands (1666 cm⁻¹), amide II band (1558 cm⁻¹) and CN (1458 cm⁻¹) bands are analyzed to assess the presence of crosslinking. Amide I bands (1666 cm⁻¹) has been attributed to C=O stretching vibrations coupled to N—H bending vibration. The amide II bands (1566 cm⁻¹) are due to the N—H bending vibrations coupled to C—N stretching vibrations. Following crosslinking of collagen, the amide bands specially amide I decreased as compared to the amide H bands in all the crosslinked samples. The reduced amide I peak relative to the amide II peak could be due to the conversion of the free —NH₂ groups in collagen to N—H groups. Increase in CN bands relative to amide I bands suggests presence of crosslinking between COOH and NH₂ groups.

The amount of amino acids released following enzymatic degradation of the crosslinked and non-crosslinked dentin-collagen was significantly different as a function of time ($p<0.05$) (FIG. 14B). After 7 days, the control group specimens disintegrated completely and released the highest amount of amino acid (5 µmol/mL). The GD group showed the highest resistance to collagenase degradation even on the 7$^{th}$ day (0.096 µmol/mL). In case of photodynamically crosslinked dentin-collagen samples using Rose Bengal, resistance to degradation was comparable to the GD group till day 3 and showed minimal increase on day 7 (0.25 µmol/mL). Chitosan polymer-Rose Bengal nanoparticles crosslinked dentin-collagen showed slightly faster degradation as compared to Rose Bengal on day 7, and which possibly associated with the degradation of chitosan. Furthermore, the interaction of chitosan and collagen was evaluated using SDS Page analysis (data not shown). The collagen samples treated with chitosan showed bands similar to the collagen control even after exposure to collagenase enzyme. This could be due to the interaction of collagen with chitosan resulting in covering of sites that are susceptible to collagenase attack. Chitosan has also been shown to neutralize matrix metalloproteinases that degrade the collagen. This could provide additional protection to collagen against enzymatic degradation.

FIG. 14C illustrates stress-strain curves demonstrating increased ultimate tensile strength and fracture toughness of all the crosslinked dentin-collagen samples compared with the non-crosslinked control samples. Even though, the GD crosslinked dentin-collagen samples showed higher increase in ultimate tensile strength the percentage elongation of the collagen-samples decreased drastically contributing to brittle behavior. The average initial toughness of collagen following demineralization was 17 MP. The samples crosslinked using GD showed reduction in toughness by almost 38%. Samples from other two treatment groups, Rose Bengal (196%) and chitosan polymer-Rose Bengal nanoparticles (281%) showed significant increase in toughness compared to the control group samples ($p<0.05$).

Figure 15:
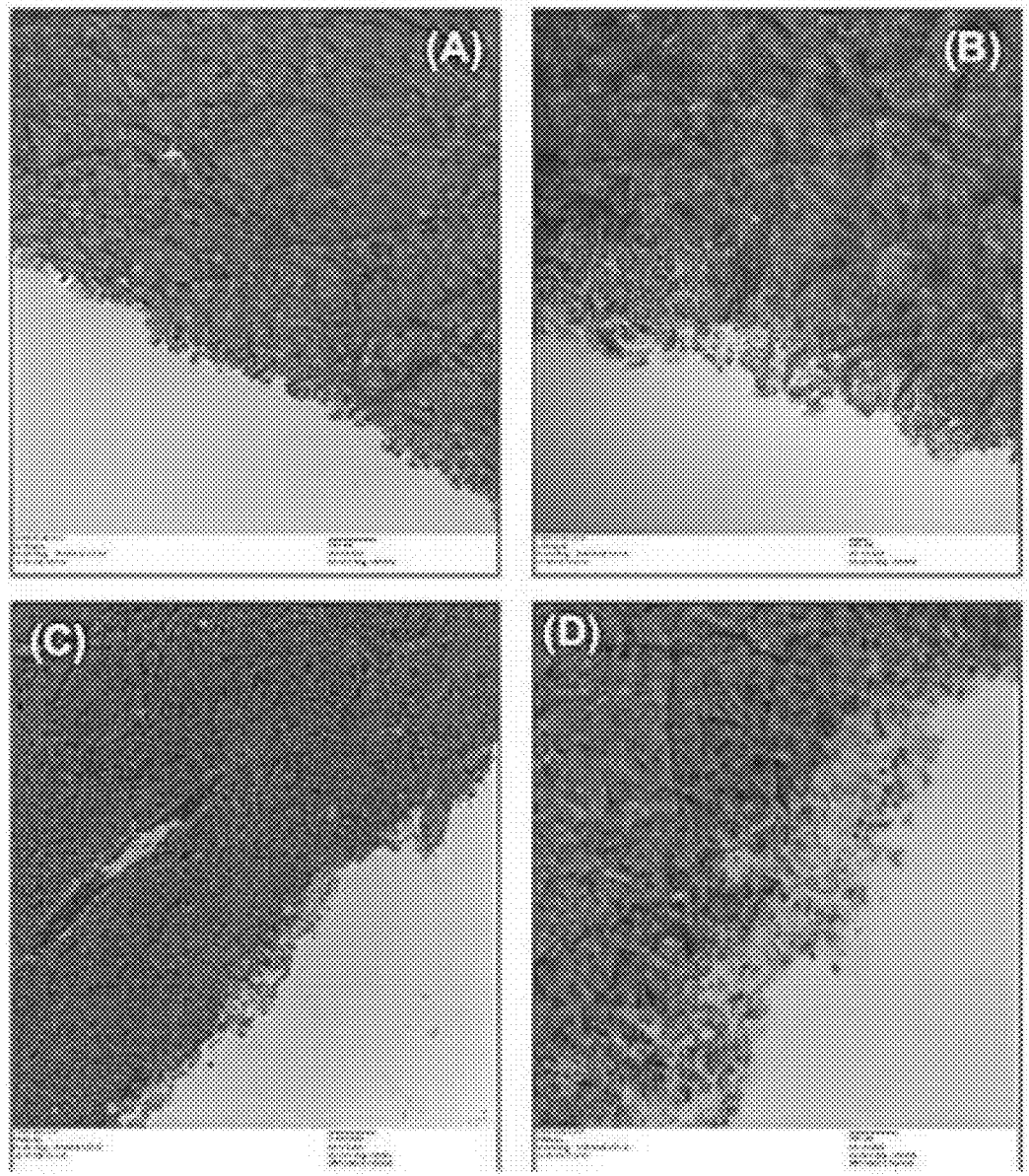
FIG. 15 shows transmission electron micrographs of dentin collagen without any treatment (A & B) and following photo-crosslinking treatment with chitosan polymer-Rose Bengal nanoparticles (C & D)

TEM micrographs from the control group revealed a collagen matrix that contained intact, banded collagen fibrils (FIGS. 15A and 15B). Following crosslinking using chitosan polymer-Rose Bengal nanoparticles, the arrangements of the collagen fibrils were denser with smooth edges (FIG. 15C). The surface of the crosslinked collagen showed a layer of collagen fibrils and nanoparticles incorporated within the collagen mesh (FIG. 15D).

Conjugation of chitosan with Rose Bengal exhibits characteristics of both polymer and photosensitizer as determined by the absorption and FTIR spectra of chitosan polymer-Rose Bengal. Where higher concentration of chitosan are used, the chitosan polymer-Rose Bengal nanoparticles conjugates are cationic in nature as a result of the free amine groups. Since higher concentrations (>0.5 mg/mL) of chitosan polymer-Rose Bengal showed aggregation by low monomer to dimer ratio, chitosan polymer-Rose Bengal nanoparticles at a concentration of about 0.01 to 0.5 mg/mL, and preferably about 0.3 mg/mL were used. The presence of a saccharide peak in FTIR and a decreased amide I peak indicates chemical conjugation of chitosan with Rose Bengal. The ability for chitosan polymer-Rose Bengal nanoparticles to produce singlet oxygen was seen as the reduction of DPBF absorbance. The rate of singlet production by chitosan polymer-Rose Bengal nanoparticles was less compared to Rose Bengal, and it is believed this may be due to the Rose Bengal bound to the polymeric chitosan nanoparticles. Chitosan is a known oxygen scavenger and may have contributed to this reduction in the release of singlet oxygen. Rose Bengal showed higher cytotoxicity with and without photodynamic therapy, however, the chitosan polymer-Rose Bengal nanoparticles showed lesser degree of cytotoxicity even after photodynamic therapy.

Chitosan Polymer Rose Bengal Nanoparticles

Chitosan polymer nanoparticles due to their cationic charge and nano-form are highly reactive towards anionic particles or surfaces. However, the time taken to exert significant antibacterial activity is comparatively long (48 hrs) and presents as an important limitation to be used clinically for root canal disinfection. In addition due to its low solubility in neutral pH, it is known to form aggregates.

PDT using different photosensitizers also possesses limitations in achieving complete disinfection of root canals. This has been contributed to the inability of PS to penetrate into the biofilm structure, self-quenching when PS is used in high concentration and remaining PS may be toxic to the host cells. The presence of serum proteins is known to reduce the antibacterial effect of PDT. Previously, it has been proposed that by modifying chitosan with Rose Bengal (RB), the particles obtained were water soluble as well as retained the PS properties.

Chitosan polymer Rose Bengal nanoparticles synthesised in accordance with the present study achieved enhanced uptake into the biofilm structure. Subsequent photoactivation of the Rose Bengal resulted in the production of singlet oxygen. The synergistic activity of chitosan nanoparticles and photosensitizers (Rose Bengal) covalently conjugated to it resulted in significant antibacterial activity as well as disruption of the biofilm structure.

Figure 16:
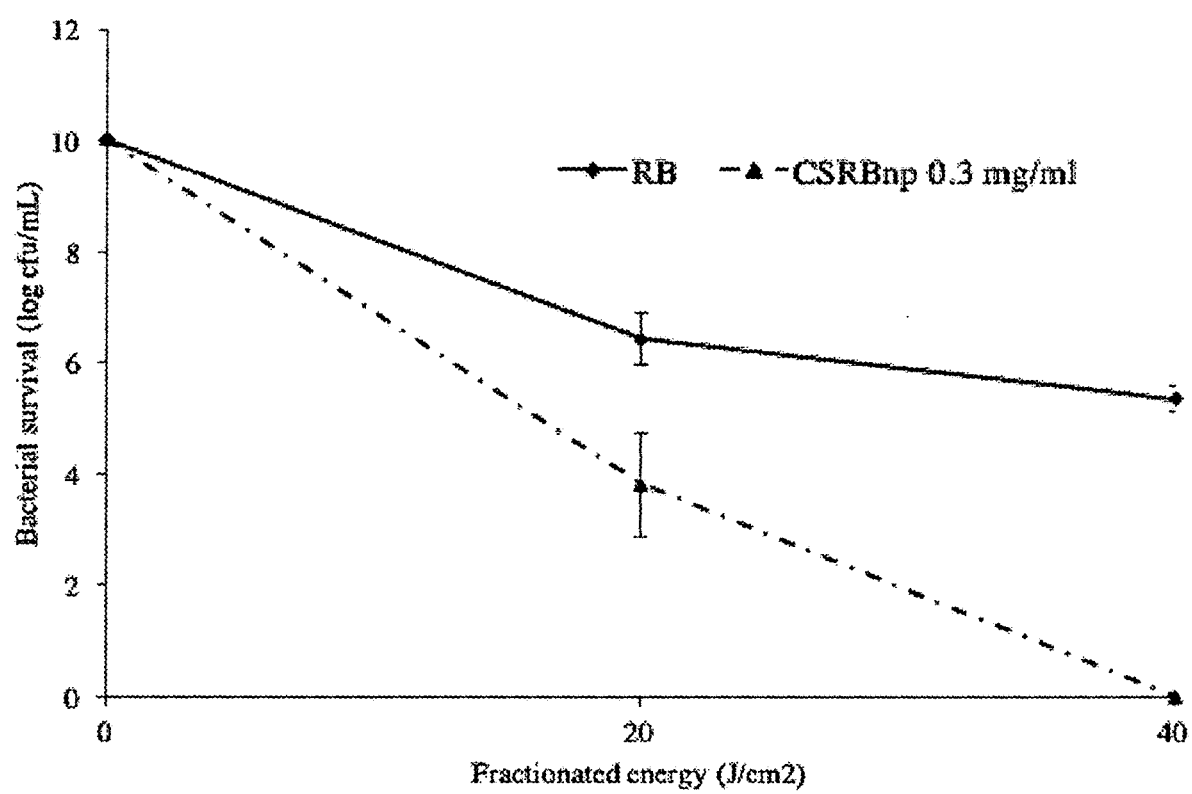
FIG. 16 shows graphically the log number of E. faecalis in biofilm forms surviving the photodynamic therapy (PDT) conducted in a multiwell plate.
Figure 17:
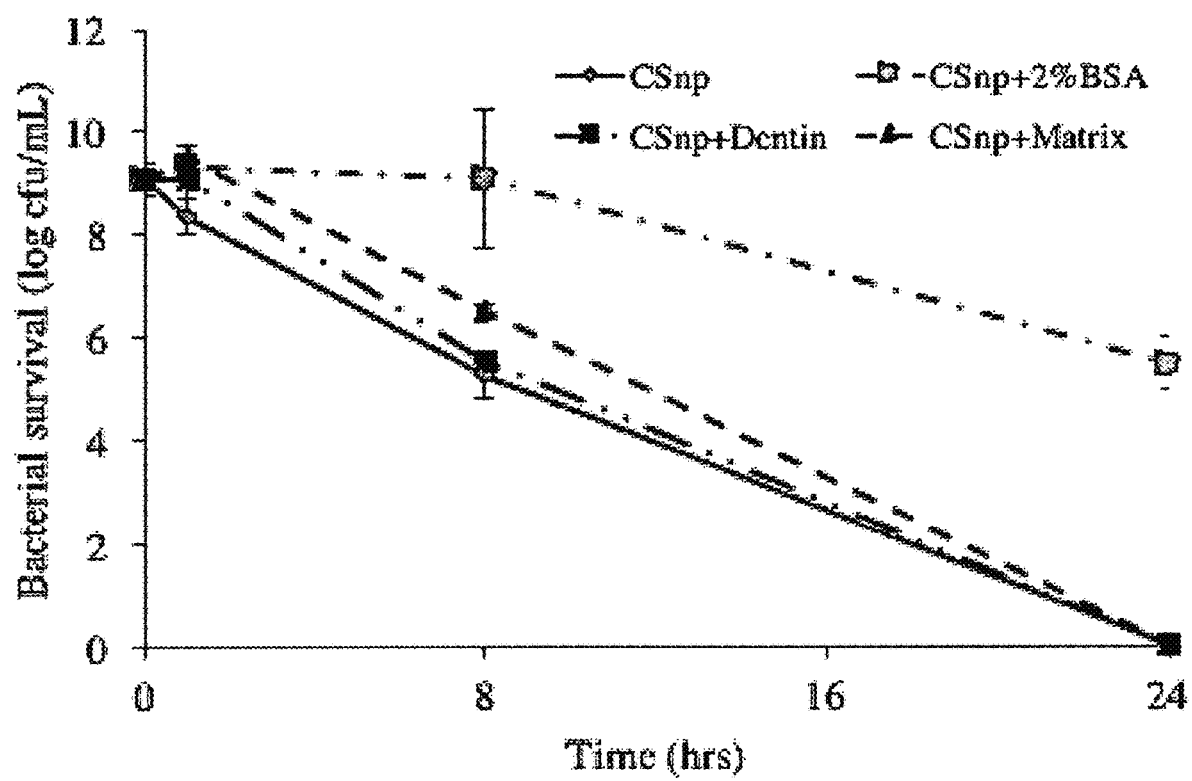
FIG. 17 shows the log number of E. faecalis in planktonic forms surviving different antibacterial treatments in the presence of tissues inhibitors. Chitosan nanoparticle effect was inhibited significantly by bovine serum albumin (BSA) 2% even following 24 hour treatment.
Figure 18:
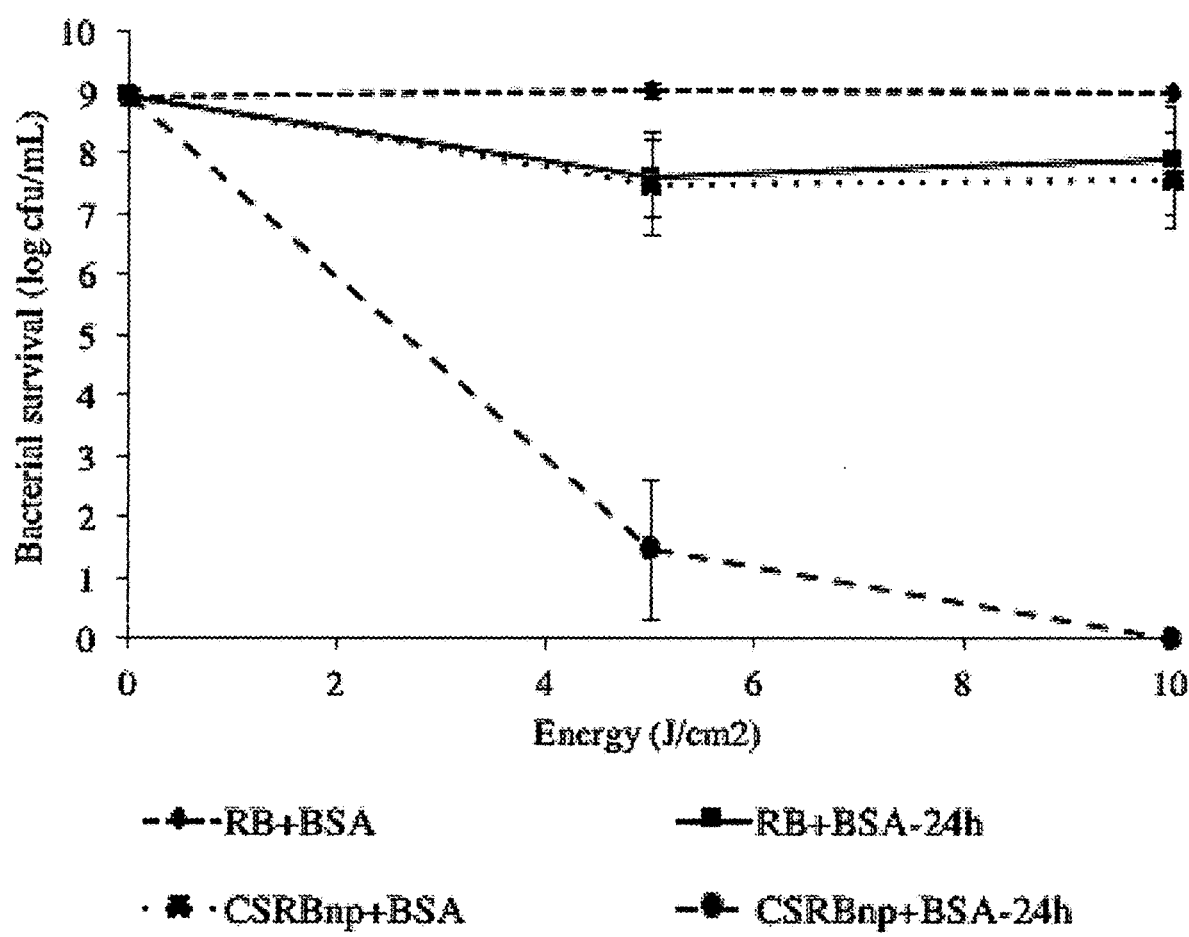
FIG. 18 shows chitosan polymer rose Bengal nanoparticles after photodynamic therapy followed by a longer period of interaction resulting in complete elimination of E. faecalis even in the presence of bovine serum albumin. Arrow bars show the standard deviation from average values.
Figure 19:
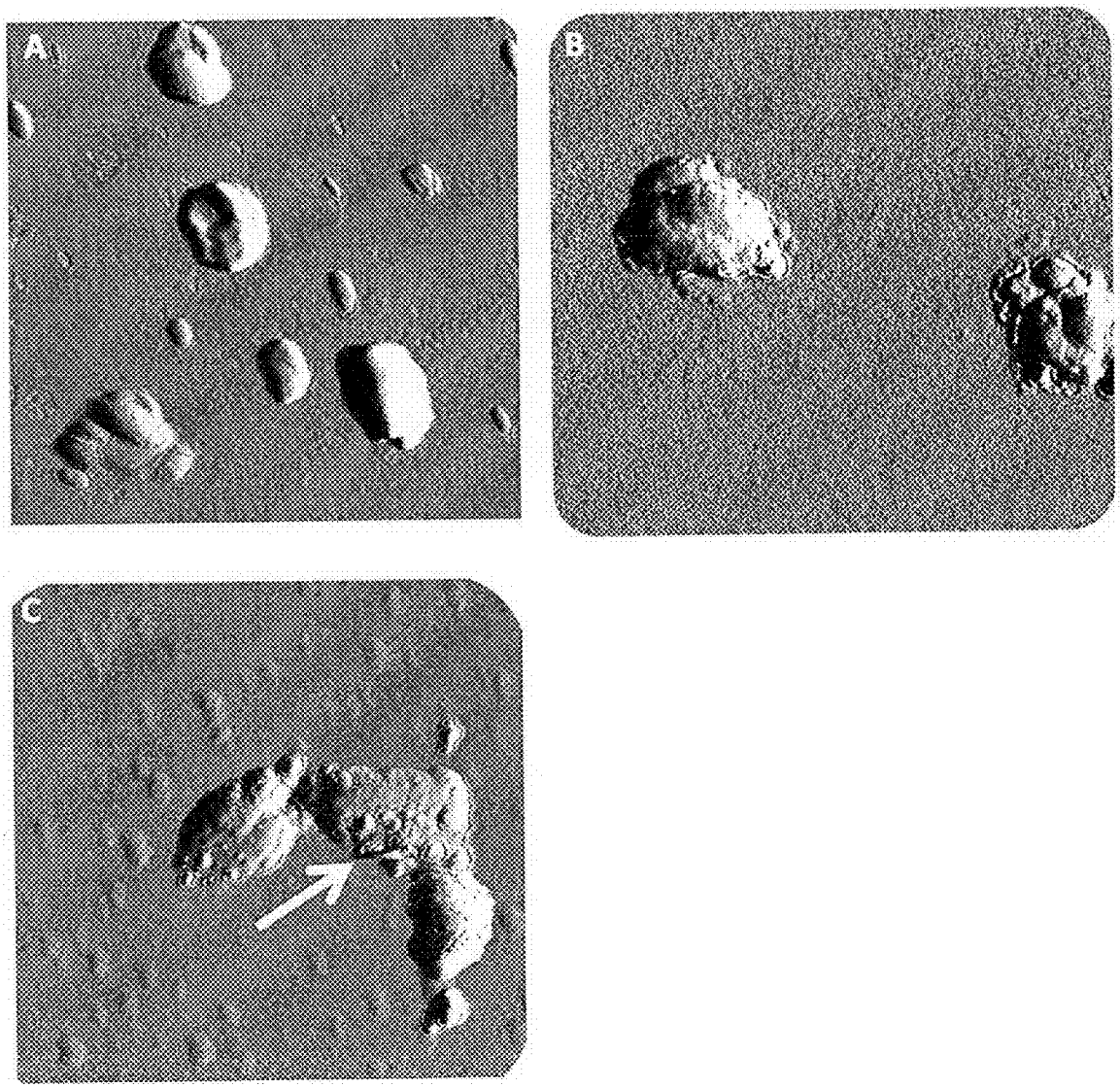
FIG. 19 shows AFM images of planktonic E. faecalis (a) control, without any treatment; (b) chitosan treated cells for 15 minutes; and (c) Chitosan polymer Rose Bengal nanoparticles treated cells for 15 minutes followed by photodynamic therapy (5 $J/CM^2$). The controlled cells showed smooth celled surface with definite cell membrane. Chitosan nanoparticle treated cells were covered by the nanoparticles and the cell surface appeared rough. Following treatment with Chitosan polymer Rose Bengal nanoparticles and photodynamic therapy, the cell surface appeared corrugated, nanoparticles were seen bound and penetrating the antibacterial cells. The cell membrane was defuse and regular, suggesting membrane damage.

In addition, as shown in FIG. 16, the effect of tissue inhibitors, such as pulp, proteins/exudates and dentine collagen matrix inhibited the antibacterial properties of chitosan nanoparticles and PDT alone. It is highly pertinent to realize the importance of dentin constituents; tissue remnants and serum products present within the root canals neutralize the commonly used antibacterial disinfectants. Similar reductions in the antibacterial activities of newer disinfection agents were also reported. Till date there is no such antibacterial agent available for root canal disinfection that is effective even in the presence of various tissue inhibitors. The chitosan conjugated Rose Bengal nanoparticles show the ability to overcome the inhibition following photoactivation and prolonged interaction time. This further supports the immediate antibacterial of PDT and the delayed antibacterial effect provided by the chitosan nanoparticles.

CONCLUSIONS

The experimental results suggest that conjugation of photosensitizers with positively charged molecules allows cationic chitosan polymer-Rose Bengal nanoparticles bound actively to negatively charged bacterial surfaces, thereby allowing enhanced penetration of the Rose Bengal through bacterial membranes. Without being bound by a particular theory, the close proximity is believed to advantageously facilitate the diffusion of singlet oxygen into the cells. In particular, singlet oxygen is known to diffuse approximately 50 nm, with the result that such close proximity would advantageously achieve more effective bacterial elimination. In addition, chitosan in itself possesses a significant broad-spectrum antimicrobial activity against bacteria, yeasts as well as viruses. Membrane damage, increased permeability and intracellular leakage are the antibacterial mechanisms of chitosan. This appears evident by the cytoplasmic release following bacterial membrane damage upon chitosan polymer-Rose Bengal nanoparticles treatment. At higher concentrations of chitosan polymer-Rose Bengal nanoparticles, the amount of cytoplasmic release is similar to that of a photodynamic therapy, suggesting the membrane damage effect of chitosan nanoparticles. Even though complete elimination of planktonic bacteria was observed with chitosan polymer-Rose Bengal nanoparticles treatment alone, biofilm bacteria showed a higher degree of resistance. Studies have shown that Rose Bengal may not completely eliminate biofilm bacteria as compared to the cationic photosensitizer methylene blue. Chitosan polymer-Rose Bengal nanoparticles combined with photodynamic therapy showed complete elimination of the biofilm, which may occur as a result of the better association of photosensitizer with the bacterial cells. The slower release of singlet oxygen by chitosan polymer-Rose Bengal nanoparticles appears to aid in the elimination of biofilm during fractionation of dosage.

The experimental results show that crosslinking delays the enzymatic degradation of dentin-collagen, and at the same time increases the overall UTS and fracture toughness. The chemical composition and presence of collagen crosslinking were confirmed using FTIR spectroscopy. The tensile testing used provided information on the mechanical properties such as UTS and toughness after chemical/photodynamic crosslinking of dentin-collagen specimens. Again, without being bound to a particular theory, the shift in peak maxima of amide I and amide II, after collagen crosslinking, has been linked to the conversion of free —$NH_2$ groups to NH groups. The increase in CN bands relative to amide I bands has been suggested as due to the crosslinking between COOH and $NH_2$ groups. The overlap of the amide bands of collagen and chitosan (1589 $cm^{-1}$) further may result in the shift in amide II following crosslinking of dentin-collagen with chitosan polymer-Rose Bengal nanoparticles. Bacterial collagenase enzymes degrade collagen by hydrolyzing the peptide bond on the aminoterminal side of Glycine (—X-Gly-Pro). Commercially available purified bacterial collagenase has been used previously to degrade collagenous tissues. Following crosslinking of collagen, the sites of collagenase attack may be hidden or modified, and this contributes to the significant difference in the release of amino acid residues following enzymatic degradation. In experimental studies, untreated control specimens showed the highest overall release of amino acid at all time points in the degradation analysis. The ultrastructure of dentin collagen also showed incorporation of chitosan polymer-Rose Bengal nanoparticles into the collagen matrix following crosslinking. Apart from improving the resistance of collagen, chitosan may play a role in neutralizing MMPs, which are known to degrade dentin-collagen.

Crosslinked collagen-specimens demonstrated improved mechanical properties with the chitosan polymer-Rose Bengal nanoparticles group showing the highest value of toughness, when compared to the merely crosslinked collagen specimens. It was found that infiltration of chitosan reinforced the collagen structure by amplifying the number of amine reaction sites resulting in the formation of ionic complexes between chitosan and collagen during crosslinking. Chitosan polymers have been considered structurally similar to extracellular matrix materials, showing controlled cell growth and reinforcing the collagen constructs. Incorporated chitosan may also serve as spacer blocks for some amine groups in collagen and prevent undesired zero-length crosslinking, to subsequently improve the fracture toughness.

Chitosan based micro and nanoparticles conjugated with photosensitizer molecules in accordance with the present invention provide various advantages in dental therapies and preferably as part of an endodontic treatment process. When activated with light (photodynamic therapy) the nanoparticles achieve the dual functions of effectively eliminating bacterial biofilms, and further result in crosslinking the dentin-collagen. The crosslinking of collagen induced by the photosensitizer molecule conjugated to the chitosan, allows for simultaneous incorporation of chitosan nanoparticles into the dentin hard tissue matrix. This advantageously improves the mechanical and chemical stability of dentin.

The experiment results also highlight the ability of phosphate group bound nanoparticles to induce biomineralization, in combination with antimicrobial properties which inhibit microbial biofilm formation within the interfaces. The nanoparticles of the present invention may advantageously be used in vivo as a step treatment strategy to treat a variety of types of infected hard tissues in clinical scenarios, wherein tissue disinfection and/or structural integrity needs to be addressed.

Although the detailed description describes the use of Rose Bengal as a photosensitizer, the invention is not so limited. It is to be appreciated that other compounds which operate to generate singlet oxygen as part of photodynamic therapies may also be used. A range of photosensitizers, either cationic or anionic could be conjugated or encapsulated using chitosan nanoparticles. Such compounds may include without restriction, flavins, methylene blue, porphyrins as well as other photosensitizers that contain free reactive group in its chemical structure. The conjugated micro/nanoparticles could target bacteria or mammalian cells depending on the application.

Although the detailed description describes the use of the nanoparticles in pre-treating dentin as part of an endodontic procedure, the invention is not so limited. The particles of the present invention could equally be used in a variety of other dental restorative applications, including, without restriction, the placement of dental filings, in crown and veneer procedures, as well as in the pre-treatment of connective tissues, for example, prior to the placement of dental implants in a patient's jaw bone.

Similarly, while the detailed description describes the use of nanoparticles as a pre-treatment material for dentin tissue, it is understood that the particles may also be used with a variety of other types of hard and connective tissues in the body, including management of dentin caries.

Although the detailed description describes and illustrates various preferred embodiments, the invention is not limited to the preferred embodiments which are disclosed. Many modifications and variations will occur to persons skilled in the art. For a definition of the invention, reference may be had to the appended claims.

The invention claimed is:

1. A method of dental treatment during a root canal treatment of a tooth within an oral cavity of a patient, comprising:
   contacting a dentin within the root canal with a therapeutic composition for 15 minutes or less, the therapeutic composition comprising a nonaggregating slurry of functionalized chitosan nanoparticles the contacting allowing the nanoparticles to incorporate into a collagen matrix of the dentin within the root canal, the nanoparticles having a first portion of the nanoparticles comprising deacetylated chitosan covalently bound to photosensitizer moieties and a second portion of the nanoparticles comprising chitosan covalently bound to phosphoryl moieties; and
   exposing the nanoparticles incorporated in the collagen matrix of the dentin within the root canal to a light having a wavelength selected to activate the photosensitizer moieties from about 2 minutes to about 10 minutes to (a) crosslink collagen of the collagen matrix within the dentin to the nanoparticles incorporated into the collagen matrix to improve tensile strength and fracture toughness of the dentin and (b) disrupt an existing biofilm in the root canal without cytotoxicity to a patient tissue of the oral cavity.

2. The method of claim 1 wherein the first portion of the nanoparticles correspond to the second portion of the nanoparticles, such that the photosensitizer moieties and the phosphoryl moieties are bound to the same biopolymer repeat unit.

3. The method of claim 1 wherein the photosensitizer moieties are any one of an anionic photosensitizer, a porphyrin, and photosensitizers that contain a free reactive group in its chemical structure, and wherein the photosensitizer moieties are selected to produce singlet oxygen upon photodynamic therapy and chemically bound to the nanoparticles without wash out.

4. The method of claim 3 wherein the photosensitizer moieties are anionic photosensitizers.

5. The method of claim 4 wherein the anionic photosensitizer is any one of rose bengal and flavin.

6. The method of claim 1, further comprising the steps of:
   removing infected pulp tissue from a tooth root and forming the root canal thereby exposing dentin along a substantial length of the root canal prior to the step of contacting the dentin with the therapeutic composition.

7. The method of claim 6, further comprising after exposing the nonaggregating slurry to the light, and filling the root canal with a filling material.

8. The method of claim 6 further comprising the step of cleaning and shaping the root canal prior to the application of the non-aggregating slurry.

9. The method of claim 1 wherein the period of time of exposure to the light inside the root canal is using light probes or carrier to activate the nanoparticles inside the root canal.

10. The method of claim 1, wherein the therapeutic composition is characterized in that it acts as an endodontic agent for pre-treatment of the dentin.

11. The method of claim 2, wherein the therapeutic composition is an antibiofilm agent for elimination of the existing biofilm inside the root canal.

12. The method of claim 1 wherein the nanoparticles are between 80 nm and 180 nm in diameter and have a positive charge of between 30 and 80 mV.

* * * * *